United States Patent
Joshi et al.

(10) Patent No.: US 11,504,485 B1
(45) Date of Patent: Nov. 22, 2022

(54) CELLULAR THERAPY INFUSION DEVICES, SYSTEMS, AND METHODS FOR USE

(71) Applicant: CELLULAR VEHICLES INC., San Mateo, CA (US)

(72) Inventors: Nikhil Joshi, San Carlos, CA (US); Marcus Foley, San Jose, CA (US); Avnesh Thakor, Menlo Park, CA (US)

(73) Assignee: CELLULAR VEHICLES, INC., San Mateo, CA (US)

( * ) Notice: Subject to any disclaimer, the term of this patent is extended or adjusted under 35 U.S.C. 154(b) by 0 days.

(21) Appl. No.: 17/824,881

(22) Filed: May 25, 2022

Related U.S. Application Data

(60) Provisional application No. 63/291,933, filed on Dec. 20, 2021, provisional application No. 63/234,426, filed on Aug. 18, 2021.

(51) Int. Cl.
| | |
|---|---|
| *A61M 5/48* | (2006.01) |
| *G16H 20/17* | (2018.01) |
| *A61M 5/315* | (2006.01) |
| *A61M 5/168* | (2006.01) |
| *A61M 5/145* | (2006.01) |

(Continued)

(52) U.S. Cl.
CPC .......... *A61M 5/484* (2013.01); *A61M 5/1456* (2013.01); *A61M 5/16854* (2013.01); *A61M 5/31511* (2013.01); *G16H 20/17* (2018.01); *A61M 2005/2086* (2013.01); *A61M 2005/3143* (2013.01); *A61M 2205/3368* (2013.01)

(58) Field of Classification Search
CPC .......... A61M 5/484; A61M 2005/3143; A61M 2005/2086
See application file for complete search history.

(56) References Cited

U.S. PATENT DOCUMENTS

| | | | |
|---|---|---|---|
| 2002/0077588 A1* | 6/2002 | Schneider | A61M 5/007 604/82 |
| 2002/0165496 A1* | 11/2002 | Thompson | A61M 5/3134 604/181 |

(Continued)

FOREIGN PATENT DOCUMENTS

WO    WO-2006087763 A1 *    8/2006    ............ A61M 39/12

OTHER PUBLICATIONS

Machine Translation of Chiba (WO 2016/087763 A1). (Year: 2016).*

*Primary Examiner* — Jenna Zhang
(74) *Attorney, Agent, or Firm* — Resonance IP Law, PC

(57) ABSTRACT

Cellular therapy infusion devices for the delivery of media including cellular therapies to a patient's tissue, cells, and/or blood include a barrel, a plunger that fits within the barrel, a syringe shaft, and a pressure relief system configured to achieve and/or maintain a desired level of pressure and/or force within the device so that cellular behavior and/or viability is not adversely impacted by the mechanical forces exerted thereon via depressing the plunger into the barrel so the cellular therapy media may be pushed from the barrel into a patient delivery device for administration to the patient. The cellular therapy infusion devices may cooperate with and/or fit into cellular therapy infusion systems designed to create and/or maintain preferred conditions for the cellular therapy media stored in the barrel and automatically administer the cellular therapy media from the cellular therapy infusion device to the patient in a steady, regulated, and/or preferred manner.

22 Claims, 20 Drawing Sheets

(51) Int. Cl.
  *A61M 5/20*     (2006.01)
  *A61M 5/31*     (2006.01)

(56) References Cited

U.S. PATENT DOCUMENTS

| | | | | |
|---|---|---|---|---|
| 2006/0111667 | A1* | 5/2006 | Matsuura | A61B 5/150221 |
| | | | | 604/93.01 |
| 2014/0350517 | A1* | 11/2014 | Dominguez | A61M 5/486 |
| | | | | 604/218 |
| 2018/0250474 | A1* | 9/2018 | Wei | A61M 5/3137 |
| 2019/0290846 | A1* | 9/2019 | McGrogan | A61M 5/3129 |
| 2021/0402098 | A1* | 12/2021 | Xu | A61M 5/31 |

* cited by examiner

170

CELLULAR THERAPY INFUSION DEVICES, SYSTEMS, AND METHODS FOR USE

RELATED APPLICATIONS

This application is a NON-PROVISIONAL of, and claims priority to U.S. Provisional Patent Application No. 63/234,426 filed 18 Aug. 2021 and entitled Cell and Gene Therapy Delivery Systems and Methods and U.S. Provisional Patent Application No. 63/291,933 filed 20 Dec. 2021 and entitled Cell and Gene Therapy Capital Delivery Systems and Accessories and incorporates both applications by reference, in their entireties, herein.

BACKGROUND

Recent innovations in the treatment of blood-based diseases including cancers such as leukemia and lymphoma that utilize engineered T-cells (CAR T-Cell Therapy) have led to tremendous excitement in the potential of cell-based therapies across a multitude of indications. Currently approved treatments typically involve intravenous delivery of cells directly to the blood stream. This method of delivery is sufficient for treating blood-based diseases given the disease target is cancerous blood cells. However, intravenous delivery of cells for treatment of solid tissue indications often results in poor engraftment and persistence of delivered cells in the target tissue, with cell yields lower than 5%. There are a few reasons for these low yields including, cells becoming trapped by the lungs or filtering organs such as the liver and spleen on their circulatory return path, cells having off-target behavior, cells experiencing a graft-vs-host immune reaction, or cells being damaged or killed by the mechanical forces they experience during delivery into the body. Damage from these forces has been described thoroughly in 3D bioprinting research, which has shown that pancreatic beta cells experience greater than 30% cell viability loss when subjected to pressures above 20 kPa. This level of pressure and subsequent shearing stress can routinely occur during injection through a syringe, which tears apart cell membranes, and/or causes cells to change protein expression. These factors may cause cells to express pro-inflammatory markers, which leads to an unintended immune cascade, an inflammatory response in patients that can lead to death. Additionally, because solid tissue cells are by nature adherent cells, they tend to clump together or adhere to the inner surfaces of devices used for delivery, which results in blockage in the delivery channel that further increases pressure and cell damage and can also result in inconsistent dosing across patients.

Cells used in cell and gene therapies are notoriously finicky and sensitive to external environmental factors, be it chemical, mechanical, or even electrical. Cell therapy administration to date has utilized off-the-shelf devices that were designed for conventional drug delivery, not for cell therapy delivery. Cells, unlike molecules used in standard drug delivery, are extremely sensitive to the mechanical stressors from their surrounding environment, and consequently can change their function, or even deteriorate, due to the method of delivery and route utilized.

SUMMARY

Exemplary cellular therapy infusion devices disclosed herein may include a barrel, a plunger sized shaped and configured to fit within the barrel, a syringe shaft, and a pressure relief system. The barrel may be sized and shaped to accept insertion of the plunger therein and may contain, or hold, a volume of cellular therapy media in, for example, liquid and/or frozen form. The plunger may have a sealing mechanism (e.g., a gasket) that interfaces with the internal walls of the barrel to make a liquid and/or air-tight seal between the sealing mechanism and the internal surface of the barrel. In some embodiments, a magnitude of force exerted by the sealing mechanism on the internal surface of the barrel may be sufficient to resist force exerted thereon by cellular therapy media changing states from, for example, a liquid form to a solid form via a freezing process and/or sufficient to prevent leaking when the cellular therapy media transitions from a frozen to a liquid phase with, for example, a reduced volume. In these embodiments, the magnitude of force exerted by the sealing mechanism on the interval surface of the barrel may act to keep all, or most, of the cellular therapy media within a cellular therapy media reservoir during, and after, the cellular therapy infusion device undergoes a freezing process. In some cases, an assembly of the barrel and the plunger is configured to allow for agitation of the volume of cellular therapy media contained within the barrel without moving the syringe shaft.

A first end of the syringe shaft may be physically coupled to and in liquid communication with the barrel and/or a portion of the barrel holding the volume of cellular therapy media. A second end of the syringe shaft may be configured to couple to another device to facilitate delivery of the cellular therapy to a patient such as a catheter or needle. In some embodiments, the second end of the syringe shaft includes a catheter coupling (e.g., a luer lock coupling) configured to couple to a catheter. In some cases, the syringe shaft may be physically coupled to the barrel via a coupling (e.g., a slip seal) that allows the barrel to rotate around the syringe shaft while the syringe shaft remains stationary so that, for example, the volume of cellular therapy media may be agitated and/or adhesion of cells and/or cellular material included within the cellular therapy media to the internal surface(s) of the cellular therapy infusion device may be prevented.

Prior to administration of the cellular therapy media to a patient, the plunger may be positioned within the barrel at a first position and an assembly of the plunger and barrel may be configured so that when the plunger is translated from the first position to a second position (via, for example, manual and/or automated depression of the plunger), force may be applied to the volume of cellular therapy media that pushes the cellular therapy media from the barrel into the syringe shaft and, in some cases, into a catheter or other patient delivery device for eventual delivery to the patient.

The pressure relief system may be physically and/or mechanically coupled to, and in communication with, the syringe shaft and may be configured to absorb force and/or pressure exerted on the volume of cellular therapy media by, for example, depression of the plunger (i.e., translation between the first and second positions) within at least one of the syringe shaft and the barrel, thereby reducing a magnitude of force and/or pressure applied to cells, or portions thereof, included within the cellular therapy media. In some cases, the pressure relief system includes a diaphragm that may be elastic and expands in shape when a force is exerted thereon. In some embodiments, the pressure relief system may be coupled to the syringe shaft via a hollow coupling and/or tube and the diaphragm may cover the lumen of the hollow coupling and/or tube in communication with syringe shaft so that pressure, or force, that is applied to the volume of cellular therapy media via, for example, translation of the plunger from the first to second position may be directed through the hollow coupling and/or tube and translated to and/or absorbed by expansion of the diaphragm within the pressure relief system. At times, the pressure relief system may include a pressure chamber cover that covers the diaphragm and provides a hollow space that the diaphragm may expand into.

In some embodiments, the pressure relief system may include a pressure dampening tip positioned at the end of plunger configured to be proximate to and/or in communication with the volume of cellular therapy media contained within the barrel. The pressure dampening tip may include one or more compliant, or flexible, components designed to deform when pressure and/or force, when is exerted thereon as may happen when, for example, the plunger is translated from the first to the second state.

In some embodiments, a barrel rotation mechanism may be positioned on a portion of an exterior surface of the barrel. The barrel rotation mechanism may be configured and positioned to cooperate with a corresponding rotation mechanism of a cellular therapy infusion system to agitate, via rotation of the barrel, the volume of cellular therapy media contained in the barrel.

In an alternative embodiment, a cellular therapy infusion device may include a barrel, a syringe shaft, and a plunger. In some cases, an internal surface of the cellular therapy infusion device or a component thereof may be coated with an adhesion-resistant coating (e.g., a low-friction or hydrophobic coating) that prevents adhesion of cells, or cellular components included within the cellular therapy media from adhering to the cellular therapy infusion device.

The barrel may be sized and shaped to accept insertion of a plunger therein and contain a volume of cellular therapy media. At times, a barrel rotation mechanism encircles a portion of an exterior surface of the barrel. The barrel rotation mechanism may be configured and positioned to cooperate with a corresponding rotation mechanism of a cellular therapy infusion system to agitate the volume of cellular therapy media contained in the barrel.

A first end of the syringe shaft may be physically coupled to and in liquid communication with the barrel and a second end of the syringe shaft may include a catheter coupling (e.g., a luer lock coupling) configured to couple to a catheter. The syringe shaft may be physically coupled to the barrel via a coupling (e.g., a slip seal) that is configured to allow the barrel to rotate around the syringe shaft while the syringe shaft remains stationary.

The plunger may be positioned within the barrel at a first position and a plunger and barrel assembly may be configured so that when the plunger is translated from the first position to a second position, force and/or pressure is applied to the volume of cellular therapy media. This force and/or pressure may push the cellular therapy media from the barrel into the syringe shaft for eventual delivery to a patient interfacing device (e.g., catheter, intravenous bag, or needle). In some embodiments, a portion of the plunger proximate to syringe shaft includes a pressure dampening tip configured to absorb pressure and/or force that otherwise would be exerted on the volume of cellular therapy media residing in the barrel when the plunger is translated from the first to the second positions.

The cell therapy delivery device may be configured so that rotation of the barrel agitates the cellular therapy media thereby preventing adhesion of cellular therapies included within the cellular therapy media to a surface of the barrel. This may be achieved by, for example, a slip seal connector between the syringe shaft and the barrel that allows the barrel to rotate about an axis while keeping the syringe shaft stationary.

In some embodiments, the cellular therapy infusion device may include a pressure relief system physically coupled to and in communication with the syringe shaft. The pressure relief system may be configured to absorb force and/or pressure (e.g., liquid pressure) within the syringe shaft and/or the barrel. The pressure relief system may include a diaphragm that expands in shape when a force is exerted thereon. At times, the pressure relief system includes a pressure chamber cover and a diaphragm that expands in shape within the pressure chamber cover when an excess force is exerted thereon.

In some embodiments, the pressure relief systems of the cellular therapy infusion devices disclosed herein may be configured, designed, and/or manufactured to hold, absorb, and/or contain a volume of cellular therapy media that expands from the syringe shaft and/or barrel during a freezing process of the cellular therapy infusion device with the volume of cellular therapy media stored therein. This holding, absorbing, and/or containing may be achieved by, for example, expansion of a diaphragm present within the pressure relief system that is in communication with the syringe shaft so that expanding (due to, for example, a freezing process) cellular therapy media stored in the barrel and/or syringe shaft may expand against the diaphragm thereby distending it until the cellular therapy media is fully expanded (e.g., frozen). By providing expanding cellular therapy media a place to expand into, the pressure relief system reduces a likelihood that the cellular therapy media will expand outside of its intended storage location within the barrel (e.g., breach a seal between the plunger and the barrel) and be contaminated and/or leak out of the cellular therapy infusion device into, for example, a cellular therapy infusion system, clinical space, or laboratory space thereby contaminating it. In these embodiments, when the cellular therapy media defrosts (e.g., prior to administration to a patient), a volume of frozen cellular therapy media held, absorbed, and/or contained by the pressure relief system may exit the pressure relief system and return to the syringe shaft and/or barrel. When the pressure relief system includes a diaphragm, the diaphragm may contract as pressure exerted thereon by the thawing cellular therapy media decreases during the thawing process.

Additionally, or alternatively, in some embodiments, the plunger may include a sealing mechanism (e.g., a gasket) configured to interface with, and exert force on, an internal surface of the barrel thereby sealing the volume of cellular therapy media within the barrel. The force exerted by the sealing mechanism on the internal surface of the barrel may be sufficient to prevent expansion of a frozen volume of cellular therapy media beyond the sealing mechanism. This may be achieved by, for example, using a sealing mechanism that exerts a force upon the internal surface of the barrel that is greater than an expected expansion force exerted by expanding (e.g., freezing) cellular therapy media on the sealing mechanism and/or plunger. In some instances, the greater force exerted by the sealing mechanism may serve to direct expansion of the cellular therapy media into the pressure relief system.

Additionally, or alternatively, in some embodiments, the plunger may include a sealing mechanism (e.g., a gasket) configured to interface with, and exert force on, an internal surface of the barrel thereby sealing the volume of cellular therapy media within the barrel wherein the sealing mechanism is configured to articulate upwards (e.g., away from the volume of cellular therapy media) when expansion force, caused by expansion of a frozen volume of cellular therapy media, is exerted thereon thereby increasing a volume of a cellular therapy reservoir in which the cellular therapy media resides to accommodate/contain the increased volume (due to, for example, freezing) of the cellular therapy media. This may be achieved by, for example, using a sealing mechanism that exerts a force upon the internal surface of the barrel that is sufficient to maintain a liquid-tight seal with the internal surface of the barrel but also allows for movement of the sealing mechanism (and therefore the plunger) within the barrel to accommodate an expanding and/or expanded volume of cellular therapy media without allowing the expanding/expanded cellular therapy media to expand beyond the sealing mechanism. At times, motion of the sealing mechanism and/or plunger relative to the barrel may be facilitated by a friction-free and/or hydrophobic compound that allows the sealing mechanism/plunger to move within the barrel without allowing the cellular therapy media to breach the sealing mechanism.

Additionally, or alternatively, in some embodiments a material used in the construction of the cellular therapy infusion device (e.g., the barrel, syringe shaft, plunger, and/or sealing mechanism) may have similar freezing and thawing properties so that the components expand and contract at the same and/or similar rates during a freezing and/or thawing process gaps between the components (which may cause leaking and/or contamination) are not formed by irregular freezing and/or thawing of the components.

Exemplary cellular therapy infusion systems disclosed herein may include an endplate, a cellular therapy infusion device an endplate for accepting and holding a cellular therapy infusion device positioned therein in place, the endplate including a catheter exit port configured, arranged, and positioned to allow a catheter coupled to the cellular therapy infusion device to exit the cellular therapy infusion system via the catheter exit port. The cellular therapy infusion device may include a barrel, sized and shaped to accept insertion of a plunger therein and contain a volume of cellular therapy media, a syringe shaft, a first end of the syringe shaft being physically coupled to, and in liquid communication with, the barrel and a second end of the syringe shaft including a catheter coupling configured to couple to a catheter. The plunger may be positioned within the barrel at a first position and may be configured so that when a compressive force is applied to the plunger, the plunger is translated from the first position to a second position thereby pushing the volume of cellular therapy media from the barrel to the syringe shaft. The system may further comprise a motor for moving a headplate mechanically coupled thereto and the headplate may be configured to apply the steady compressive force to the plunger responsively to movement of the motor. The steady compressive force may translate the plunger from the first position to the second position.

In some embodiments, the cellular therapy infusion system may further include a thermometer configured to measure a temperature within the cellular therapy infusion system and a heat source. The heat source may be coupled to the thermometer and/or an intervening processor and the heat source may be configured to generate heat responsively to a temperature measured by the thermometer and/or an instruction from the processor (upon receipt of a temperature measurement from the thermometer) that a temperature within the system is below a threshold value. Additionally, or alternatively, the cellular therapy infusion system may include an agitation mechanism configured to agitate the volume of cellular therapy media.

BRIEF DESCRIPTION OF DRAWINGS

The present invention is illustrated by way of example, and not limitation, in the figures of the accompanying drawings in which.

Figure 1A:
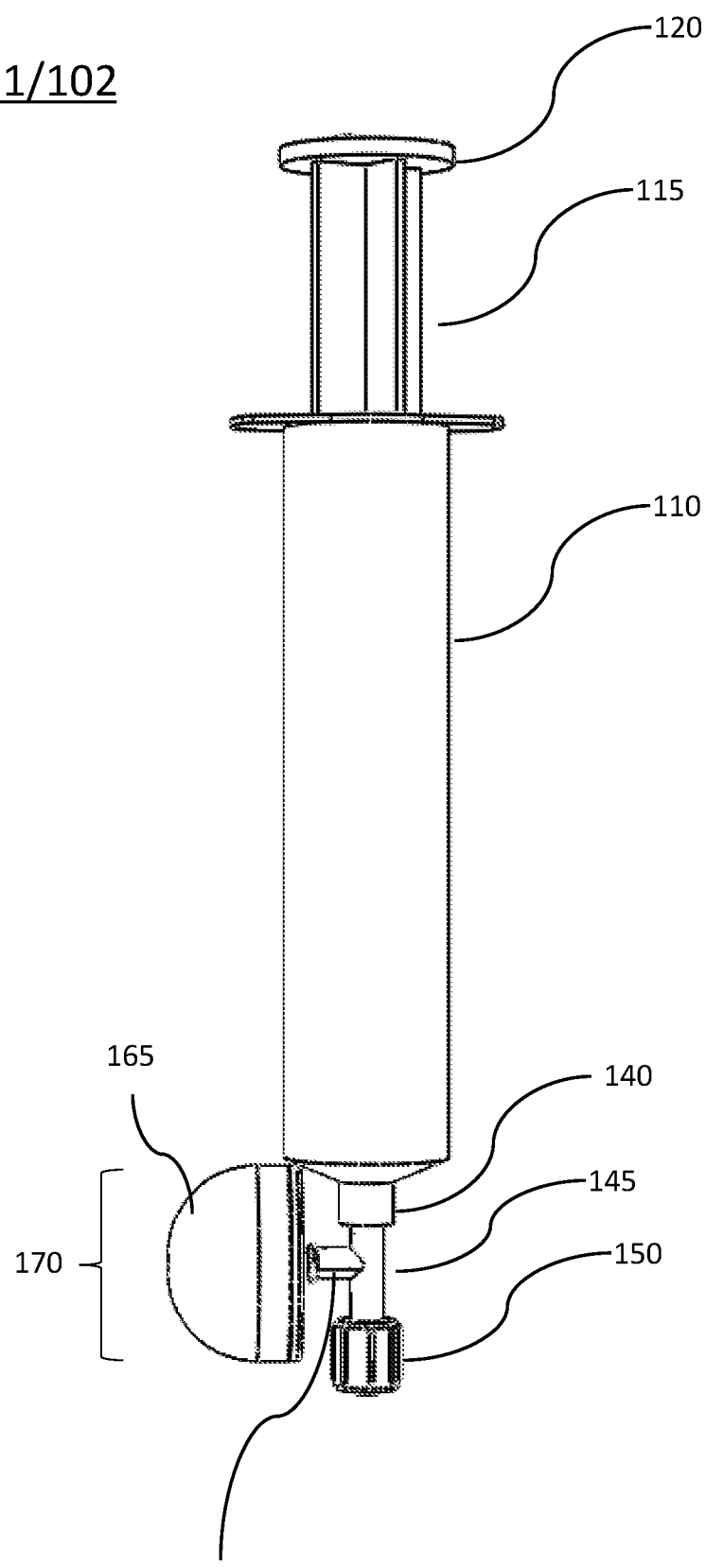
FIG. 1A provides a side view of a first or second exemplary cellular therapy infusion device with a pressure relief system, in accordance with some embodiments of the present invention.

Throughout the drawings, the same reference numerals and characters, unless otherwise stated, are used to denote like features, elements, components, or portions of the illustrated embodiments. Moreover, while the subject invention will now be described in detail with reference to the drawings, the description is done in connection with the illustrative embodiments. It is intended that changes and modifications can be made to the described embodiments without departing from the true scope and spirit of the subject invention as defined by the appended claims.

WRITTEN DESCRIPTION

The present invention is directed to, among other things, systems, devices, and methods for atraumatically delivering media (e.g., saline, reagents, blood, etc.) including and/or infused with cellular therapies and/or living therapeutic agents such as cells, genetic therapy vectors, and/or viruses (collectively referred to herein as "cellular therapies") via direct routes of access (ROA) to target tissue without damaging, altering, or killing the cellular therapies during the delivery process. The present invention achieves these objectives by, for example, maintaining optimized conditions for the cellular therapies both prior to and during the delivery process when the cellular therapy is administered to a patient and/or patient tissue. In some cases, the conditions for cell therapies included in the cellular therapy media are optimized by minimizing stressors exerted on the cellular therapies included in a media during the administration process by, for example, reducing, or eliminating, shear stress, compressive force, pressure, and/or material interactions (e.g., clumping and/or sticking of the cellular therapies to delivery devices) between delivery devices and the cellular therapies during administration to a patient. This minimization of stressors exerted on the cellular therapies may reduce a likelihood of an alteration in cellular therapy behavior, viability, concentration, and/or dosage delivered to patient tissue so that, for example, a prescribed dosage and/or type of cellular therapy is properly delivered to the patient tissue.

In some embodiments, the systems and devices disclosed herein may be configured to infuse cellular therapy into a patient's body (e.g., tissue or blood) over time and, in these embodiments, the systems and devices disclosed herein may have a relatively small (e.g., less than a cubic foot) and light weight (e.g., 3-20 kg) form factor to, for example, enable portability and/or use by a patient's bedside.

In some embodiments, the cellular therapy infusion devices may be associated with an identifier such as an optical, alpha-numeric, and/or binary code that may be matched to a type of cellular therapy and/or cellular therapy media included within the cellular therapy infusion device 100, a particular patient or type of patient (e.g., a patient with a particular diagnosis), and/or an indication for use of the cellular therapy.

Figure 1B:
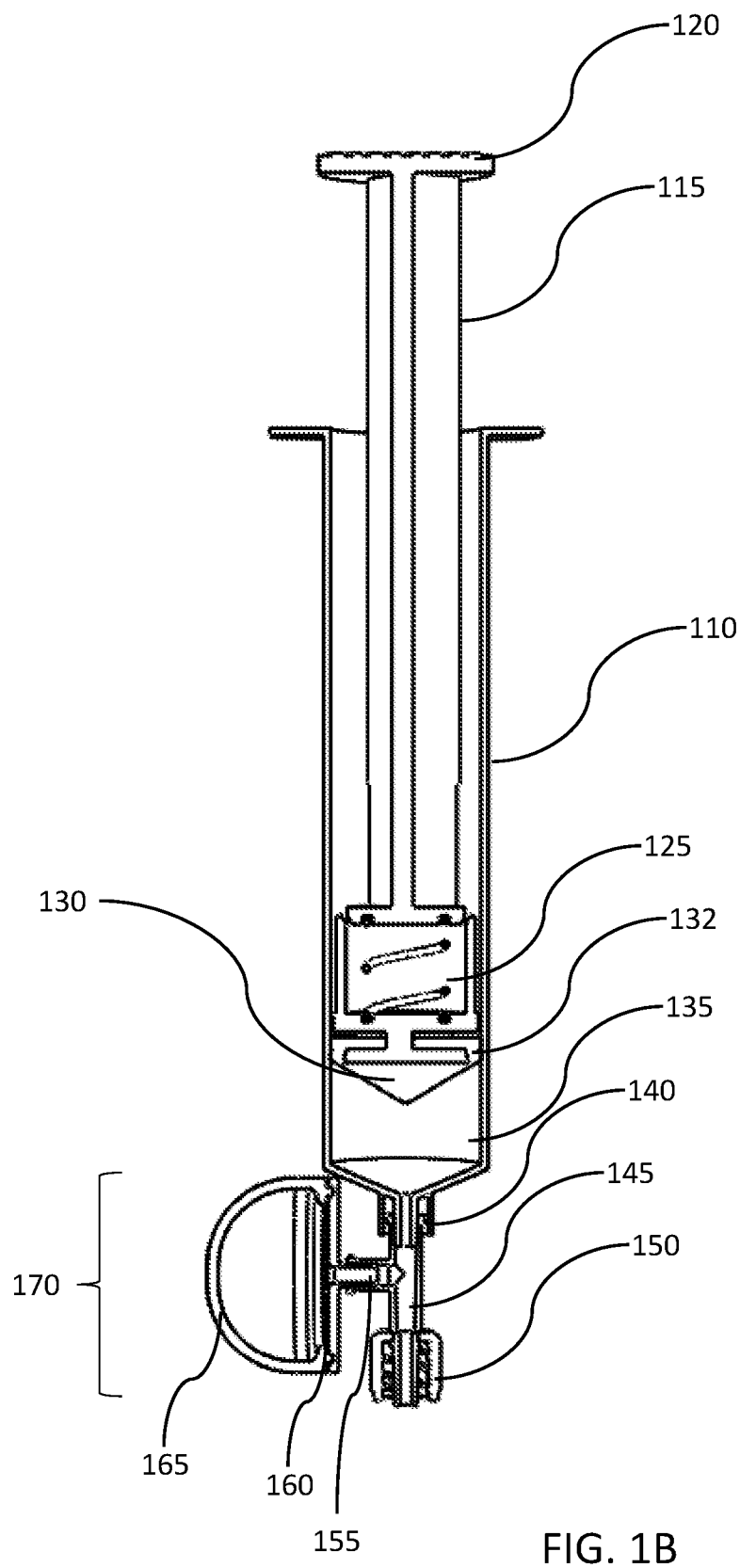
FIG. 1B provides a cross-section view of a first exemplary embodiment of a cellular therapy infusion device with a pressure relief system, in accordance with some embodiments of the present invention.
Figure 1C:
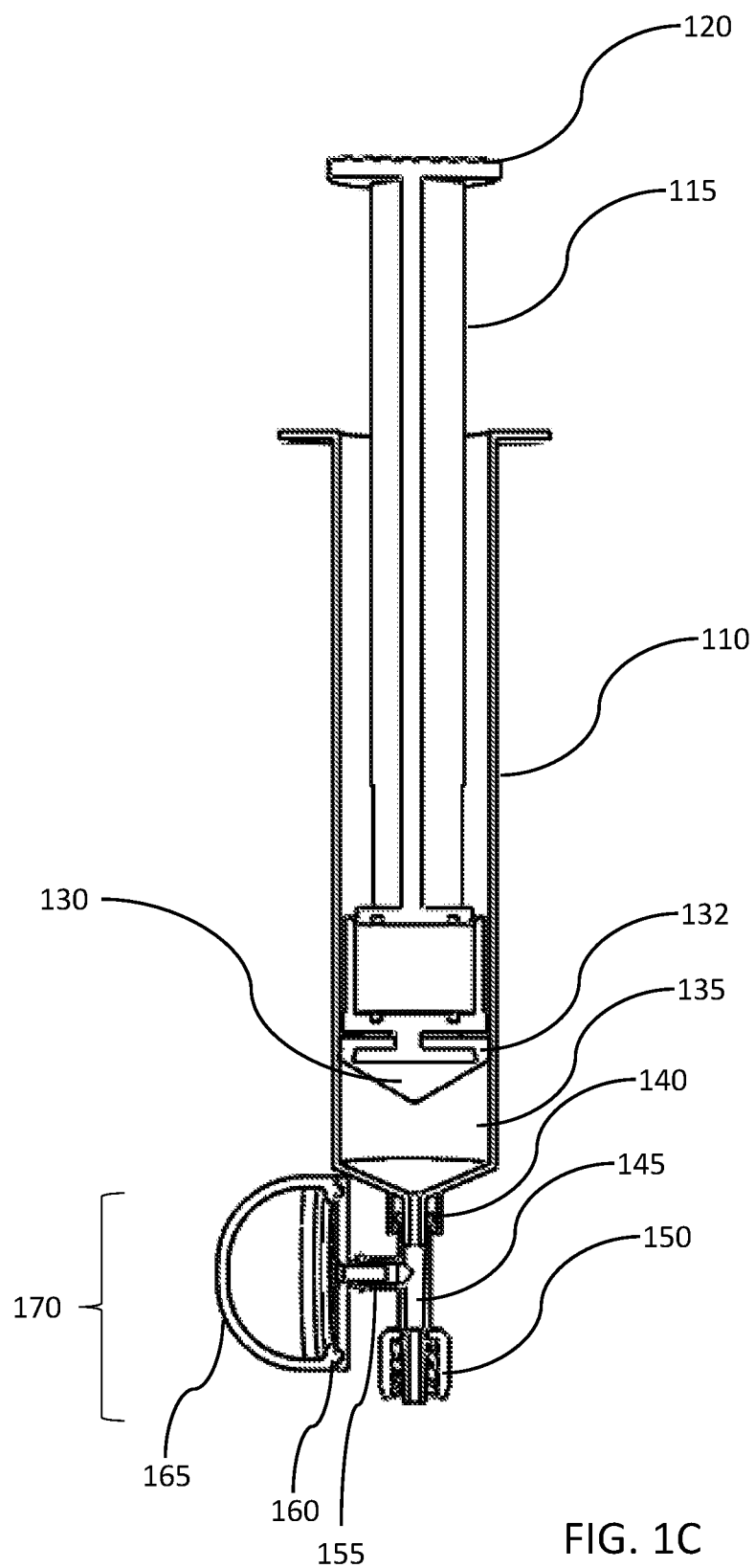
FIG. 1C provides a cross-section view of a second exemplary embodiment of a cellular therapy infusion device with a pressure relief system, in accordance with some embodiments of the present invention.

Turning now to the figures, FIG. 1A provides a side view of a first and/or second exemplary cellular therapy infusion device 100/101, FIG. 1B provides a cross-section view of first exemplary cellular therapy infusion device 100, and FIG. 1C provides a cross-section view of second exemplary cellular therapy infusion device 101. Cellular therapy infusion device 100 may be configured, designed, and manufactured to deliver media (e.g., saline, blood, reagents, etc.) that includes a number of cellular therapies (e.g., cells, bacteria, viruses, etc.) to a patient in an optimized manner that preserves, for example, initial, and/or prescribed, parameters (e.g., cellular therapy count, cellular therapy viability, cellular therapy behavior, and/or cellular therapy byproduct production) for the cellular therapy. A size, shape, and/or configuration of cellular therapy infusion device 100 may be adapted and/or configured to accommodate varying volumes of cellular therapy media, different types of cellular therapies that may be infused into a patient, and/or different delivery modalities for delivery of the cellular therapy to the patient.

Cellular therapy infusion device 100 includes a barrel 110, a plunger 115, a plunger end 120, an optional pressure/force dampening mechanism 125, an optional pressure dampening tip 130, a gasket 132, a cellular therapy media reservoir 135, a barrel/shaft coupling 140, a syringe shaft 145, a catheter coupling 150, and a pressure-relief system 170 that includes a pressure-relief system coupling 155 and a pressure chamber cover 165. Gasket 132 may form a liquid-tight seal between plunger 115 and the internal surface walls of barrel 110. In some embodiments, barrel 110, plunger 115, plunger end 120, and gasket 132 may cooperate in a manner similar to a piston so that as plunger 115 is pushed into barrel 110, cellular therapy media stored within barrel 110 (e.g., in cellular therapy media reservoir 135) may be pushed through barrel 110 into syringe shaft 145 and out of cellular therapy infusion device 100 into a patient delivery device (not shown) such as a catheter.

On some occasions, an interior surface of one or more components (e.g., barrel 110, plunger 115, optional pressure/force dampening mechanism 125, optional pressure dampening tip 130, gasket 132, barrel/shaft coupling 140, shaft 145, and/or catheter coupling 150) of cellular therapy infusion device 100 may comprise (e.g., be manufactured with a material infused with) and/or be coated with a substance that inhibits friction and/or adherence of therapeutic cells to a surface thereof, which may assist a clinician with understanding a count, or dosage, of therapeutic cells delivered to a patient because few, if any, of the living agents included in the media may adhere to the cellular therapy infusion device 100 and/or not be delivered to the patient. On some occasions, the coating may be, for example, a protein coating configured to reduce cell-material interactions, reduce cell retention, and/or clumping of cells within barrel 110. Additionally, or alternatively, the coating may be a hydrophobic and/or non-stick coating (e.g., polytetrafluoroethylene) that prevents cellular/cellular therapy and/or media adhesion.

Barrel 110 may be sized and configured to hold a volume of cellular therapy media in, for example, cellular therapy media reservoir 135 and accommodate actuation of plunger 115 from a first position as seen in FIGS. 1A and 1B wherein cellular therapy media reservoir 135 is full to a second position, wherein plunger 115 is pushed downward (as oriented in FIGS. 1A and 1B) so that cellular therapy media stored in cellular therapy media reservoir 135 is pushed through shaft 145 and into a catheter (shown in, for example, FIGS. 4B and 5A) via translation of plunger 115 from the first position to the second position. Cellular therapy media reservoir 135 may be sized and/or configured to hold, for example, 0.1 mL-50 mL of cellular therapy media. Exemplary dimensions for barrel 110 are an outer diameter of 10-45 mm an inner diameter of 8-43 mm, and a length of 60-200 mm. Exemplary dimensions for plunger 115 are an outer diameter of 8-43 mm and a length of 70-300 mm. In many embodiments, a seal, via, for example, gasket 132 and/or engagement of optional pressure/force dampening mechanism 125 and/or optional pressure dampening tip 130 with an inner diameter of barrel 110, may be present between plunger 115 and barrel 110. This seal may be air- and/or water-tight and may function to direct motion of cellular therapy media (in response to compressive force exerted therein by motion of plunger 115 from the first to the second position) through syringe shaft 145 when plunger 115 is depressed within barrel 110 (i.e., moved from the first position to the second position).

In some embodiments, one or more dimensions (e.g., diameter, length, shape) of barrel 110 relative to one or more dimensions (e.g., diameter and/or length) of syringe shaft 145 may be designed to limit turbulence and/or shearing forces exerted on the cellular therapy media. For example, a diameter of syringe shaft 145 may be 15-40% of the diameter of barrel 110 and this relatively large diameter syringe shaft may provide for a more gradual transition (which reduces turbulence and/or shearing forces exerted on the cellular therapy media) from barrel 110 to syringe shaft 145. Additionally, or alternatively, a transition from the inner diameter of barrel 110 to the inner diameter of syringe shaft 145 may be tapered to be made more gradual, in order to, for example, avoid a large pressure difference and subsequent increase in turbulent flow and shear stress while the volume of cellular therapy media is moving from cellular therapy media reservoir 135 into syringe shaft 145.

In some embodiments, barrel/shaft coupling 140 may be configured as a radial, or slip, seal that allows for rotation of barrel 110 and plunger 115 about a central axis without rotating syringe shaft 145, pressure-relief system 170, and/or catheter coupling 150. For example, barrel/shaft coupling 140 may be a slip seal connector. Additionally, or alternatively, catheter coupling 150 may be a luer connection configured and/or arranged to couple to a catheter as shown in, for example, FIG. 4B.

Optional pressure/force dampening mechanism 125 may comprise a spring or spring-like (e.g., capable of compression and expansion) material that optionally may be covered, or enclosed within, a covering. When cellular therapy infusion device 100 and/or plunger 115 is being manually actuated from the first position to the second position, optional pressure/force dampening mechanism 125 may be configured to decouple force applied to plunger 115 (via, e.g., pushing on plunger end 120) by a user from a volume of cellular therapy media contained within cellular therapy media reservoir 135 by adding a spring and/or spring-like material in series with the force applied by the user, which may have the effect of dampening, or smoothing out, the force applied to the cellular therapy media due to the user's pushing on the plunger. In some embodiments, the spring and/or spring-like material included within optional pressure/force dampening mechanism 125 thereby regulates a magnitude of force (e.g., compressive force) and/or stress (e.g., shear stress) exerted on the cellular therapy media by reducing pressure, or force, exerted on the cellular therapy media by, for example, approximately 25%-50%. A degree of the reduction of pressure, or force, exerted on the cellular therapy media may be set by, for example, a spring constant and/or length of the spring/spring-like material included in optional pressure/force dampening mechanism 125.

Optional pressure dampening tip 130 may be designed, configured, and/or manufactured, to absorb, regulate, dampen, and/or reduce compressive force and/or shear stress on a volume of cellular therapy media as plunger is translated from the first to the second position (i.e., depressed into barrel 110). In some instances, optional pressure dampening tip 130 may comprise a compliant and/or deformable material that deforms once a threshold magnitude of pressure, force, and/or stress within barrel 110 and/or cellular therapy media reservoir 135 is reached. In some embodiments, optional pressure dampening tip 130 may be designed and manufactured to cooperate with optional pressure/force dampening mechanism 125 to regulate, dampen, and/or reduce compressive force and/or shear stress on a volume of cellular therapy media as plunger is translated from the first to the second position.

Pressure-relief system 170 may be in communication with syringe shaft 145 and/or may be configured to regulate, dampen, and/or reduce fluid pressure and/or compressive force on a volume of cellular therapy media as it is pushed from cellular therapy media reservoir 135 into syringe shaft 145 via translation of plunger 115 from the first to the second position and, in this way, may prevent an application of force and/or pressure on the cellular therapy media that may, for example, induce a change in cellular therapy behavior and/or viability. As shown in FIG. 1E-1H, pressure-relief system 170 may include a diaphragm 160 that covers a base 161 of pressure relief system, wherein base 161 is in communication with pressure-relief system coupling 155 via a central aperture 180 in communication with pressure-relief system coupling 155.

As shown in FIG. 1C, second exemplary cellular therapy infusion device 101 is similar to first exemplary cellular therapy infusion device 100 with the exception that second exemplary cellular therapy infusion device 101 does not include optional pressure/force dampening mechanism 125.

Figure 1D:
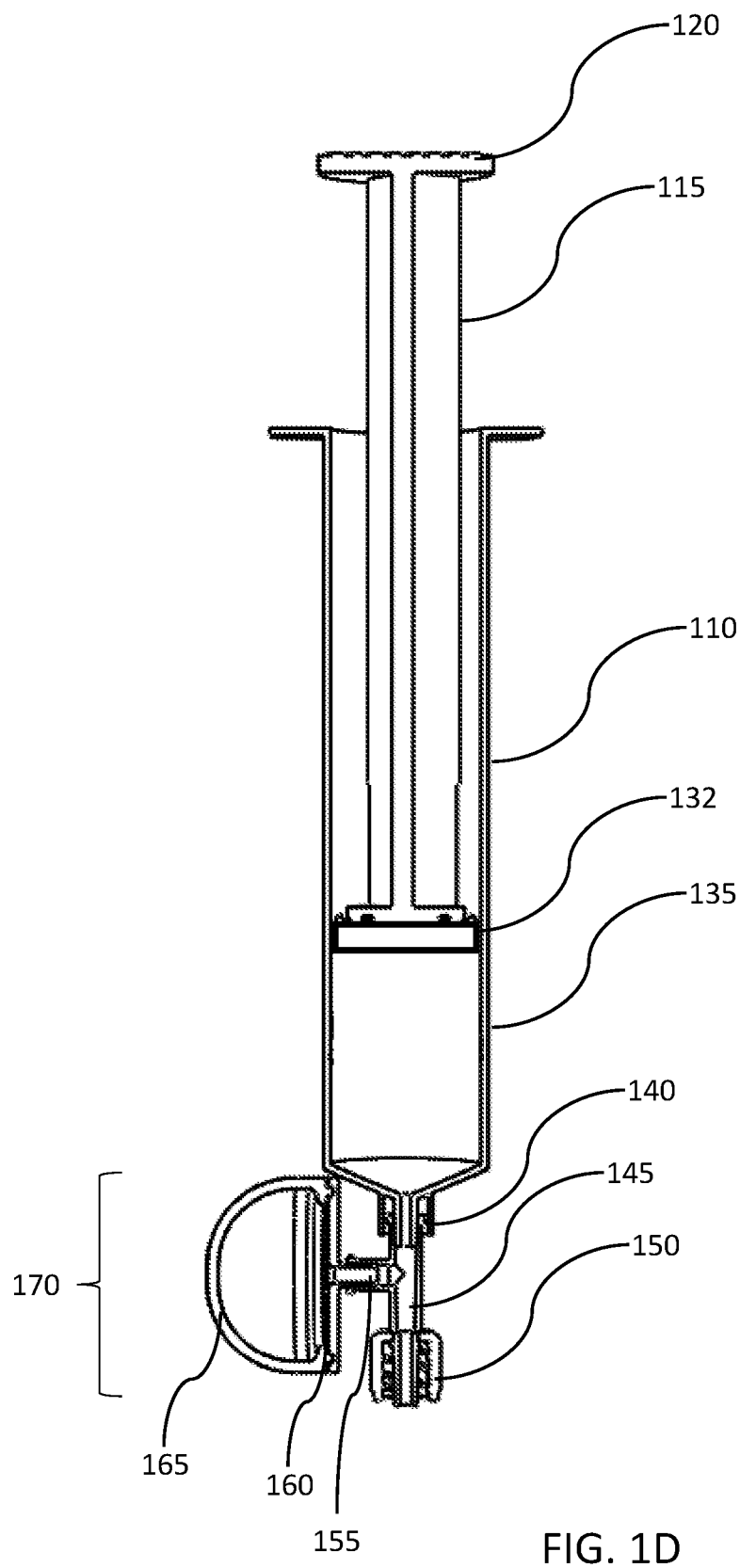
FIG. 1D provides a cross-section view of a third exemplary embodiment of a cellular therapy infusion device with a pressure relief system, in accordance with some embodiments of the present invention.

As shown in FIG. 1D, third exemplary cellular therapy infusion device 101 is similar to first exemplary cellular therapy infusion device 100 with the exception that third exemplary cellular therapy infusion device 101 does not include optional pressure/force dampening mechanism 125 and optional pressure dampening tip 130 and, instead, plunger 115 and gasket 132 are directly proximate to cellular therapy media reservoir 135. In this embodiment, pressure relief system 170 is configured to absorb/relieve any excess pressure exerted on the cellular therapy media contained within cellular therapy media reservoir 135 without the need for optional pressure/force dampening mechanism 125 and optional pressure dampening tip 130.

Figure 1E:
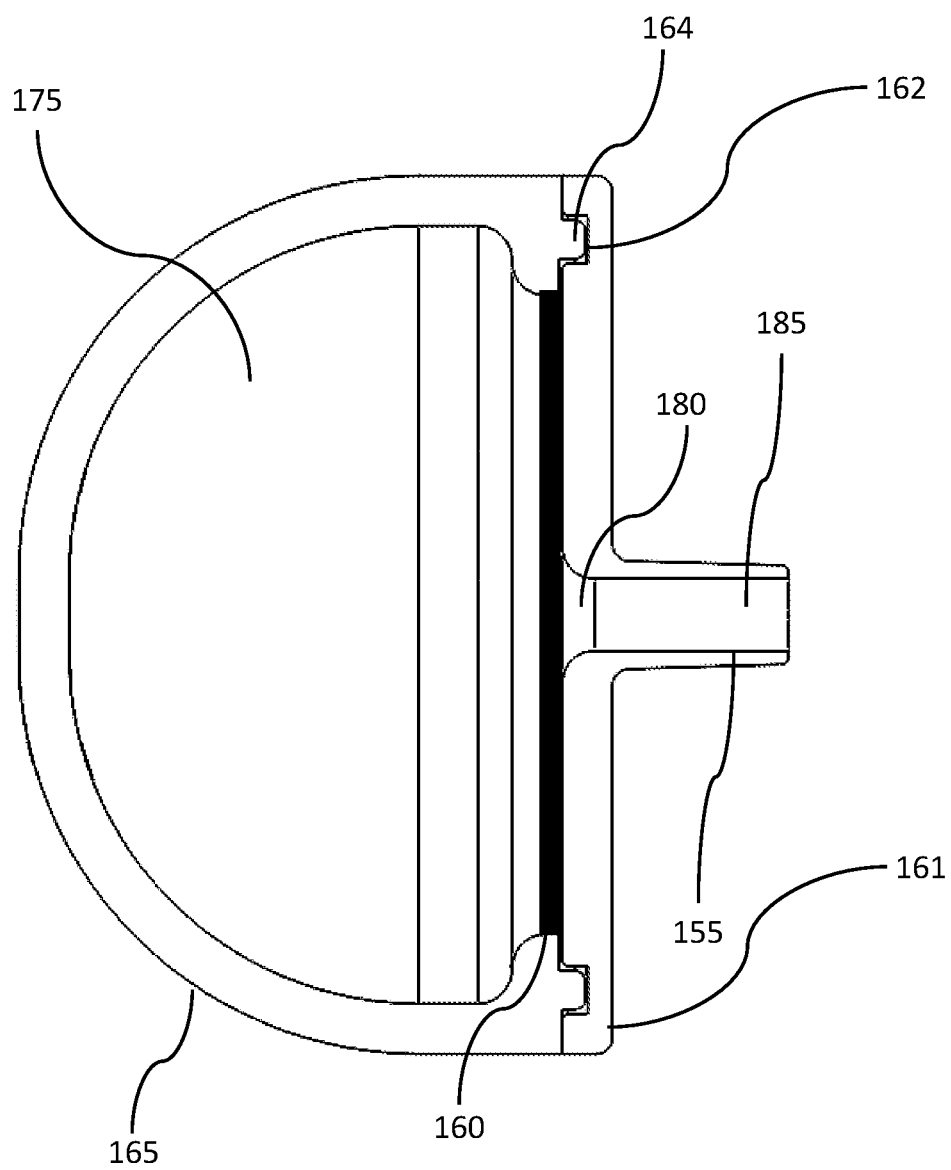
FIG. 1E is a side cross-section view of a pressure-relief system when a diaphragm is in a resting or non-distended state, in accordance with some embodiments of the present invention.
Figure 1F:
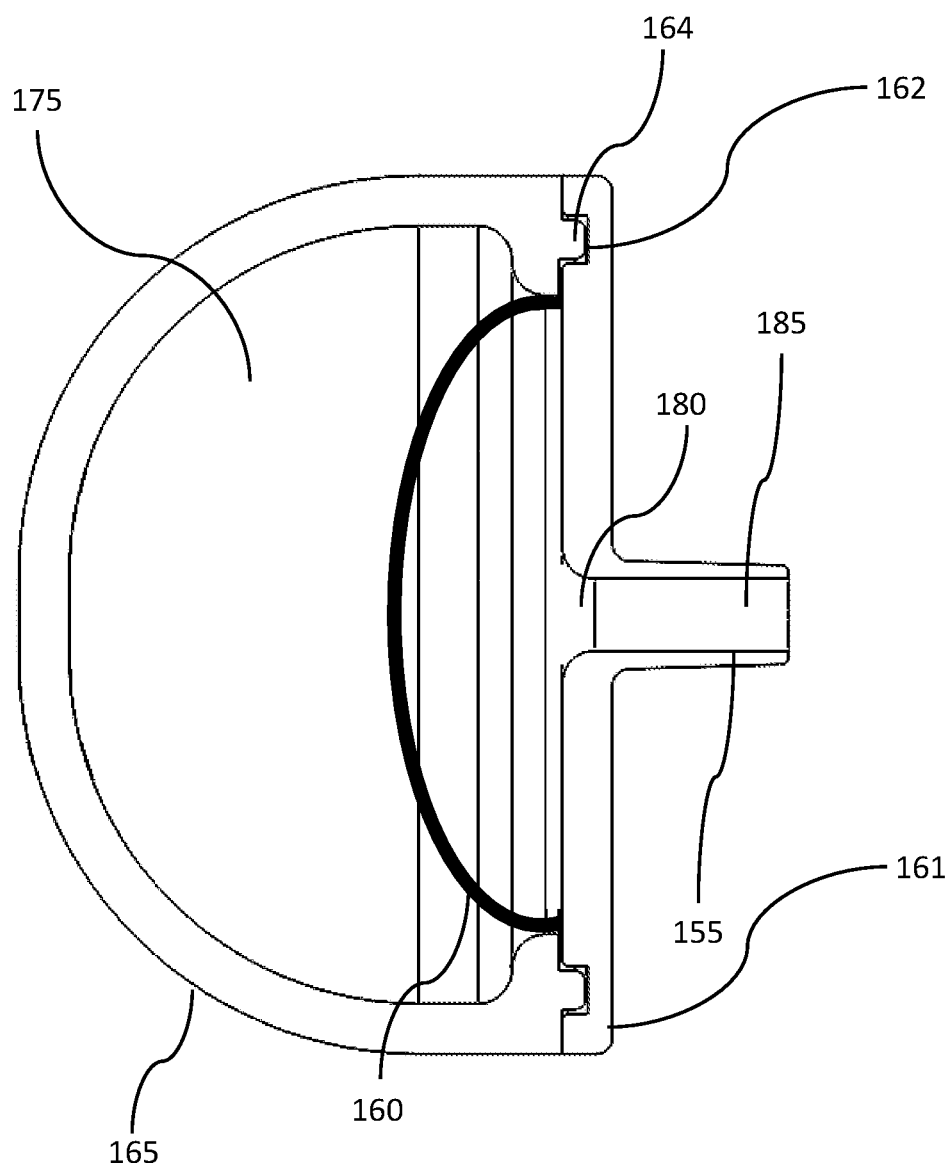
FIG. 1F is a side cross-section view of the pressure-relief system when the diaphragm is in an expanded or distended state, in accordance with some embodiments of the present invention.
Figure 1G:
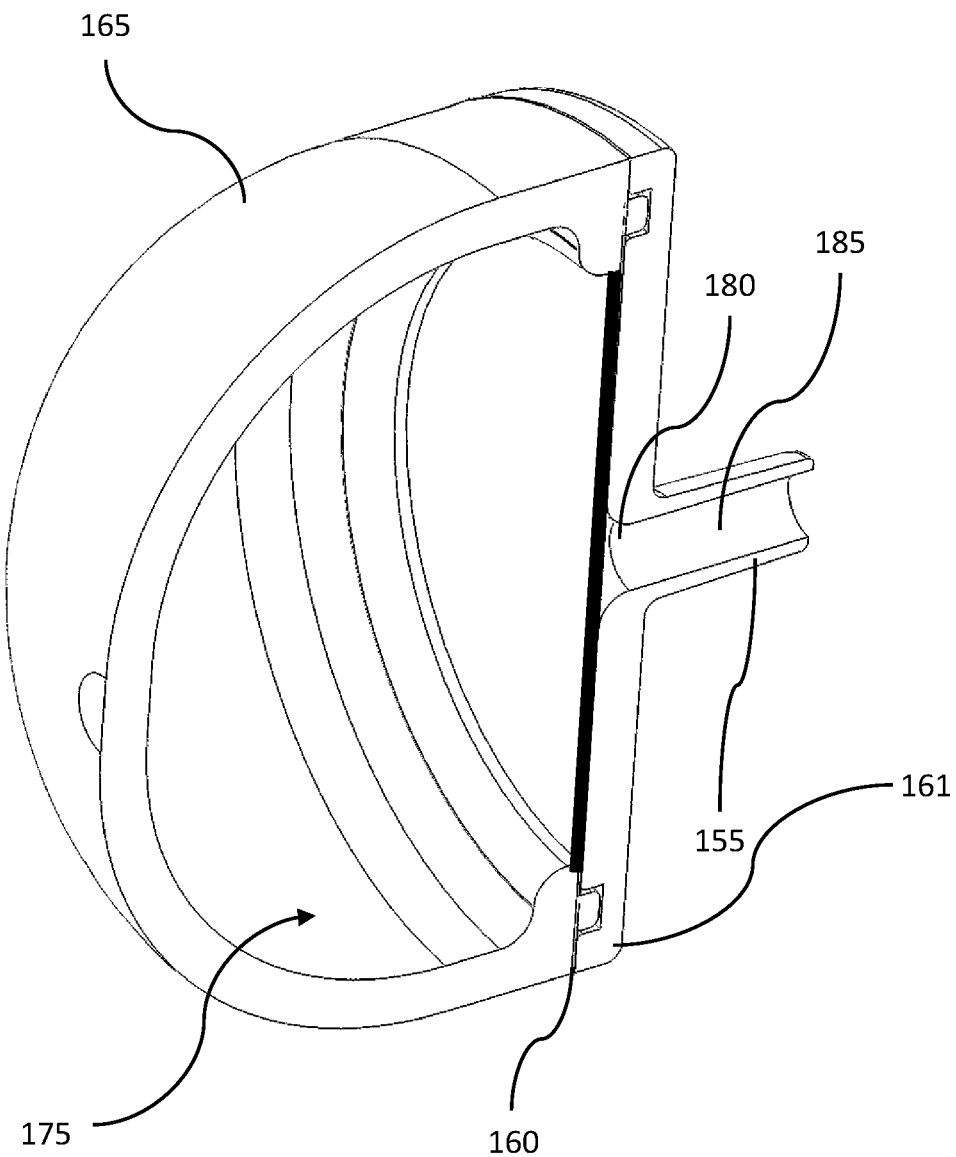
FIG. 1G is a perspective cross-section view of the pressure-relief system when the diaphragm is in a resting or non-distended state, in accordance with some embodiments of the present invention.
Figure 1H:
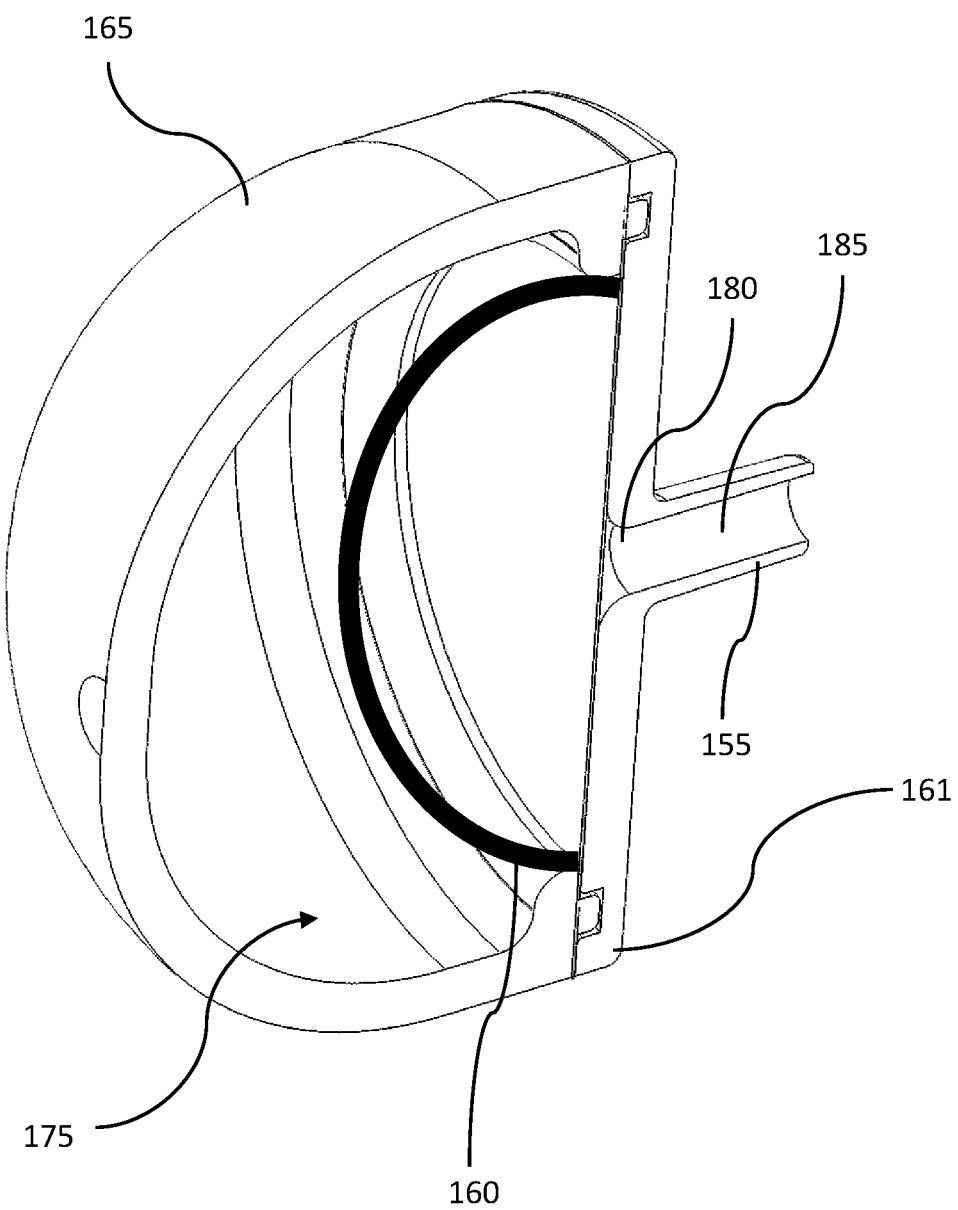
FIG. 1H is a perspective cross-section view of the pressure-relief system when the diaphragm is in the extended or distended state, in accordance with some embodiments of the present invention.

As may be seen in FIG. 1E, which is a side cross-section view of pressure-relief system 170 when diaphragm 160 is in a resting or non-distended state, FIG. 1F, which is a side cross-section view of pressure-relief system 170 when diaphragm 160 is in an expanded or distended state, FIG. 1G, which is a perspective cross-section view of pressure-relief system 170 when diaphragm 160 is in a resting or non-distended state, and/or FIG. 1H, which is a perspective cross-section view of pressure-relief system 170 when diaphragm 160 is in the extended or distended state, pressure-relief system 170 may include a hollow pressure chamber 175 that is bounded by pressure chamber cover 165. Pressure chamber cover 165 may be rigid or flexible and may have an extension 164 configured to fit within a groove 162 of a base 161 of pressure-relief system 170. Extension 164 may be inserted into and affixed within groove 162 as shown in FIG. 1E via any acceptable means including, but not limited to, mechanical, heat, and/or chemical bonding. Central aperture 180 may be in communication with a lumen 185 of pressure-relief system coupling 155 that is in communication with a lumen present within syringe shaft 145.

Diaphragm 160 may comprise an elastic or compliant material (e.g., latex or silicon) configured to expand, or distend, in response to pressure/force exerted thereon via, for example, liquid moving through syringe shaft 145, and return to an original shape/state when the pressure/force has been removed.

Figure 4A:
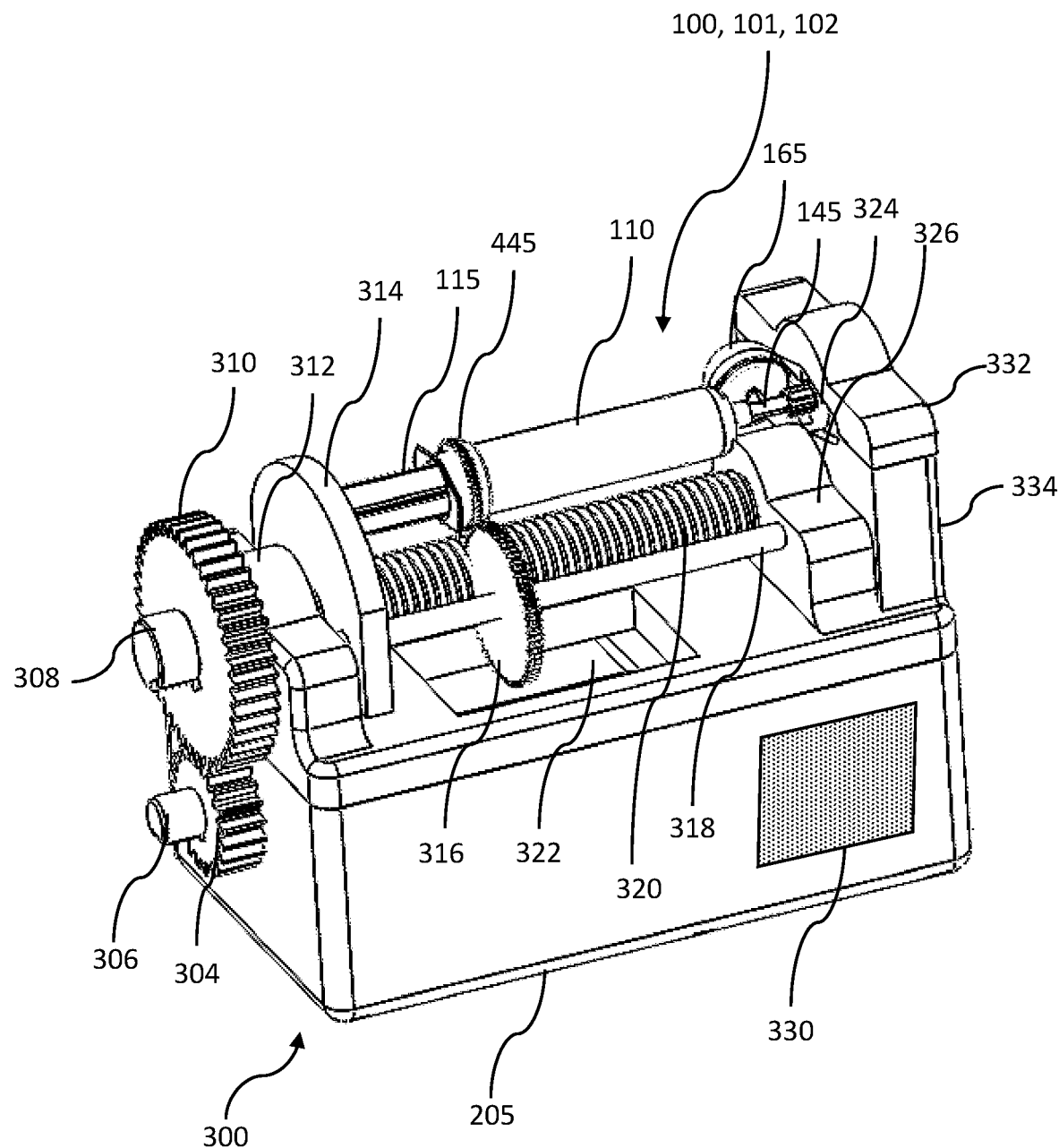
FIG. 4A is a side-perspective view of an exemplary cellular therapy infusion system with a cellular therapy infusion device positioned therein, in accordance with some embodiments of the present invention.
Figure 4B:
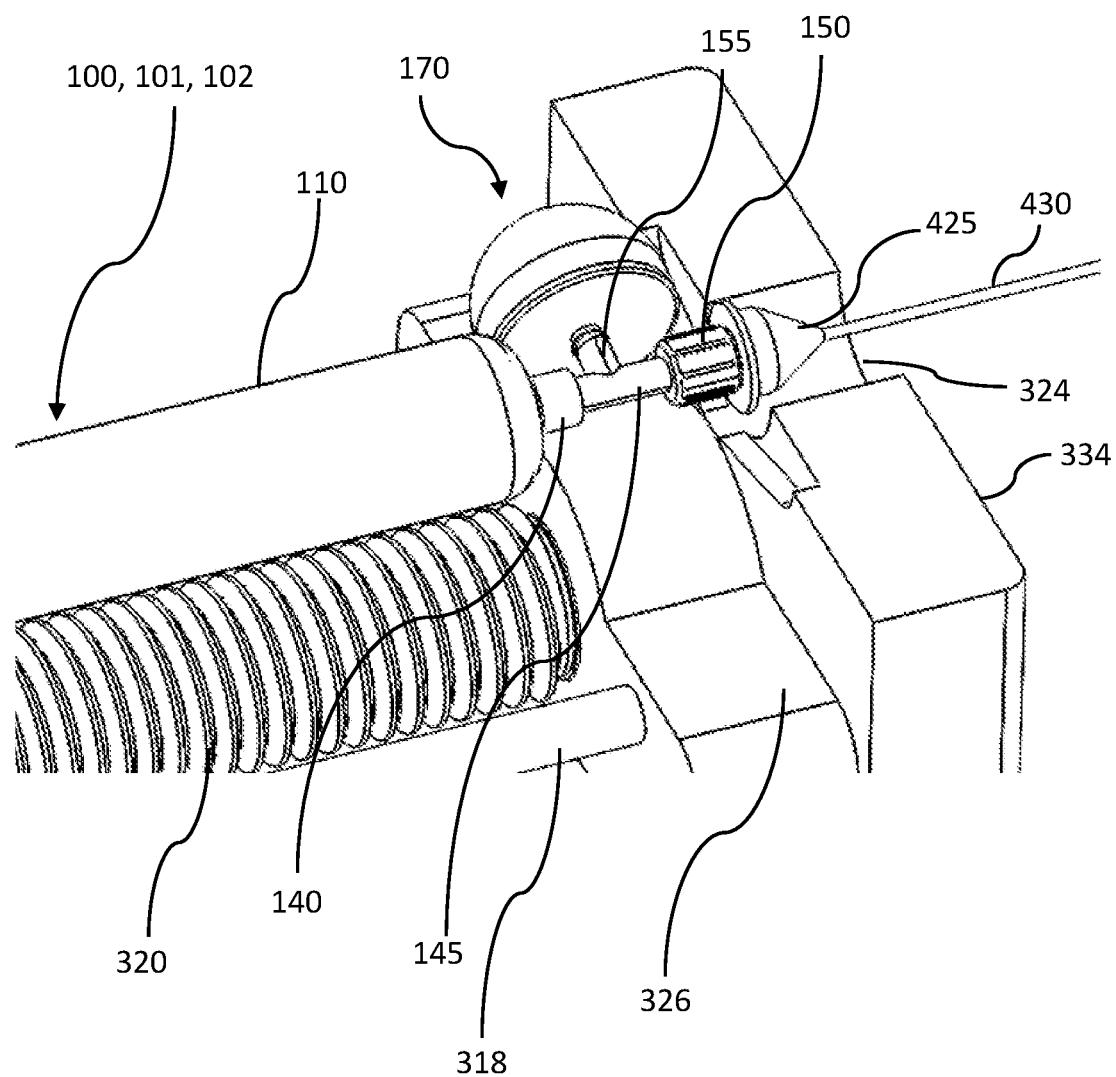
FIG. 4B is a close-up view of a portion the exemplary cellular therapy infusion system with a cellular therapy infusion device positioned therein of FIG. 4A, in accordance with some embodiments of the present invention.

Pressure relief system 170 may absorb fluid pressure and/or compressive force within the cellular therapy infusion device 100, 101, and/or 102 via expansion of diaphragm 160 into hollow pressure chamber 175 so that as pressure in barrel 110 and/or syringe shaft 145 increases when force is exerted on plunger 115 as plunger 115 translates from the first to the second position (i.e., is pushed down in to barrel 100), diaphragm 160 may expand into pressure-relief chamber 175 to temporarily increase a volume of a sub-system of cellular therapy reservoir 135 and syringe shaft 145 thereby reducing pressure within the sub-system as cellular therapy media from cellular therapy media reservoir 135 is advanced into syringe shaft 145 and/or a catheter coupled to syringe shaft 145 (as shown in FIG. 4B). As pressure and/or force within barrel 110 and/or syringe shaft 145 decreases, diaphragm 160 may elastically return to its original and/or resting configuration, thus restoring an original volume of the device/system. In some embodiments, pressure-relief system 170 may cooperate with optional pressure/force dampening mechanism 125 and/or optional pressure dampening tip 130 to dampen, regulate, and/or maintain application of a desired level of liquid pressure to cellular therapy media.

In some embodiments, a volume of cellular therapy media may be manually and/or mechanically drawn into cellular therapy media reservoir 135 via, for example, inserting an open end of syringe shaft 145 into the cellular therapy media and extracting plunger 115 from barrel 110 (i.e., moving from the second (or depressed) position to the first position). Additionally, or alternatively, a cellular therapy infusion device 100 may be prepared by, for example, the manufacturer of the cellular therapy infusion device and/or or laboratory manufacturing the cellular therapy media to be pre-loaded with cellular therapy media present in cellular therapy media reservoir 135. On these occasions, the cellular therapy media may be inserted into barrel 110/cellular therapy media reservoir 135 at a manufacturing facility and/or lab that, for example, prepares the cellular therapy media. The pre-loaded cellular therapy infusion device 100 may be placed in sealed packaging, frozen, and provided to a medical facility for use with a patient for the delivery of the cellular therapy media to the patient.

In some embodiments, cellular therapy infusion device 100 may be configured, designed, and/or manufactured so that it may be frozen with a volume of cellular therapy media contained within cellular therapy media reservoir 135. This may allow for easy transfer of a cellular therapy infusion device 100 pre-loaded with cellular therapy media between, for example, a lab, cellular therapy manufacturing facility, and/or a refrigerated repository (e.g., hospital freezer) and an environment in which the cellular therapy is administered to the patient without compromising cellular viability and/or altering cellular behavior.

To achieve a cellular therapy infusion device 100 in which a volume of cellular therapy media may be pre-loaded into cellular therapy media reservoir and frozen, the cellular therapy infusion device 100 may be adapted and/or designed to accommodate for the expansion of the cellular therapy media during the freezing process and/or the expansion and/or contraction of materials of which components of cellular therapy infusion device 100 is made so that, for example, expansion of cellular therapy media while transitioning between the liquid and solid states does not push past gasket 132 of plunger 115 and into a portion of barrel 110 located above gasket 132. This may be achieved via using components that have similar freezing and/or thawing characteristics as they transition between being from being frozen (e.g., −5 degrees Celsius) to non-frozen (e.g., 20-40 degrees Celsius) and/or from being non-frozen to frozen so that no gaps are formed between components that may freeze and/or thaw at different rates. Additionally, or alternatively, prevention of frozen cellular therapy media escaping from cellular therapy media reservoir 135 may be achieved by using a wide gasket 132 and/or a gasket 132 configured to exert a relatively large amount of lateral force on the internal surface of barrel 110 and this lateral would counter any force applied by expanding cellular therapy media (as may occur during the freezing process) thereby keeping cellular therapy media within cellular therapy media reservoir.

Figure 1I:
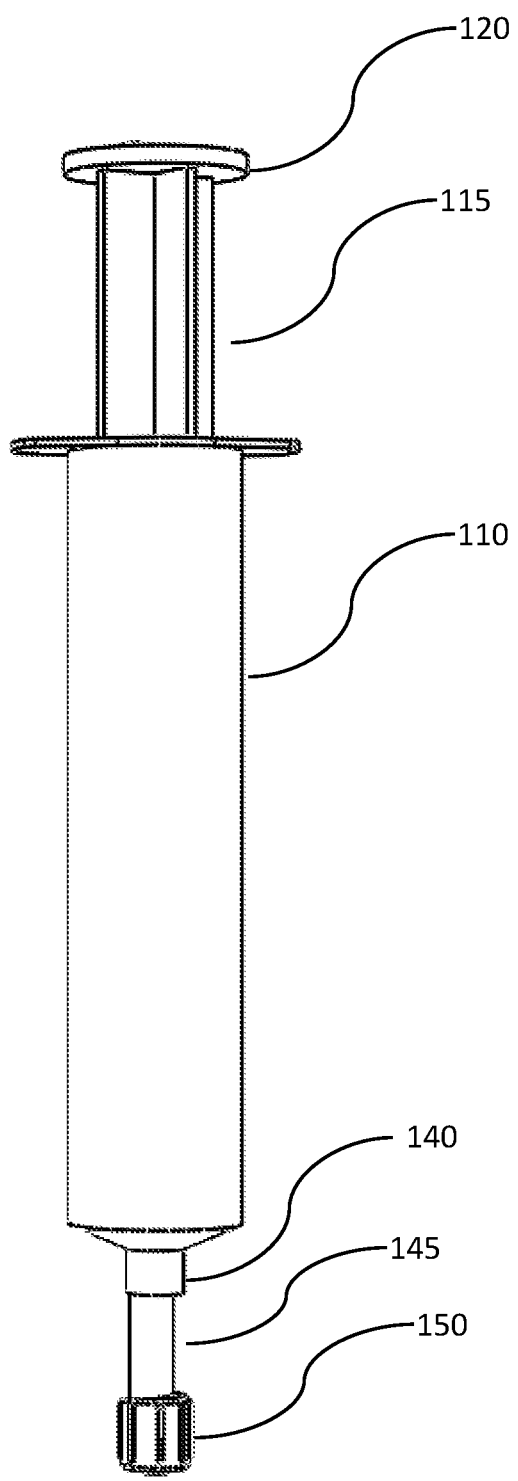
FIG. 1I provides a side view of a fourth exemplary cellular therapy infusion device, in accordance with some embodiments of the present invention.
Figure 1J:
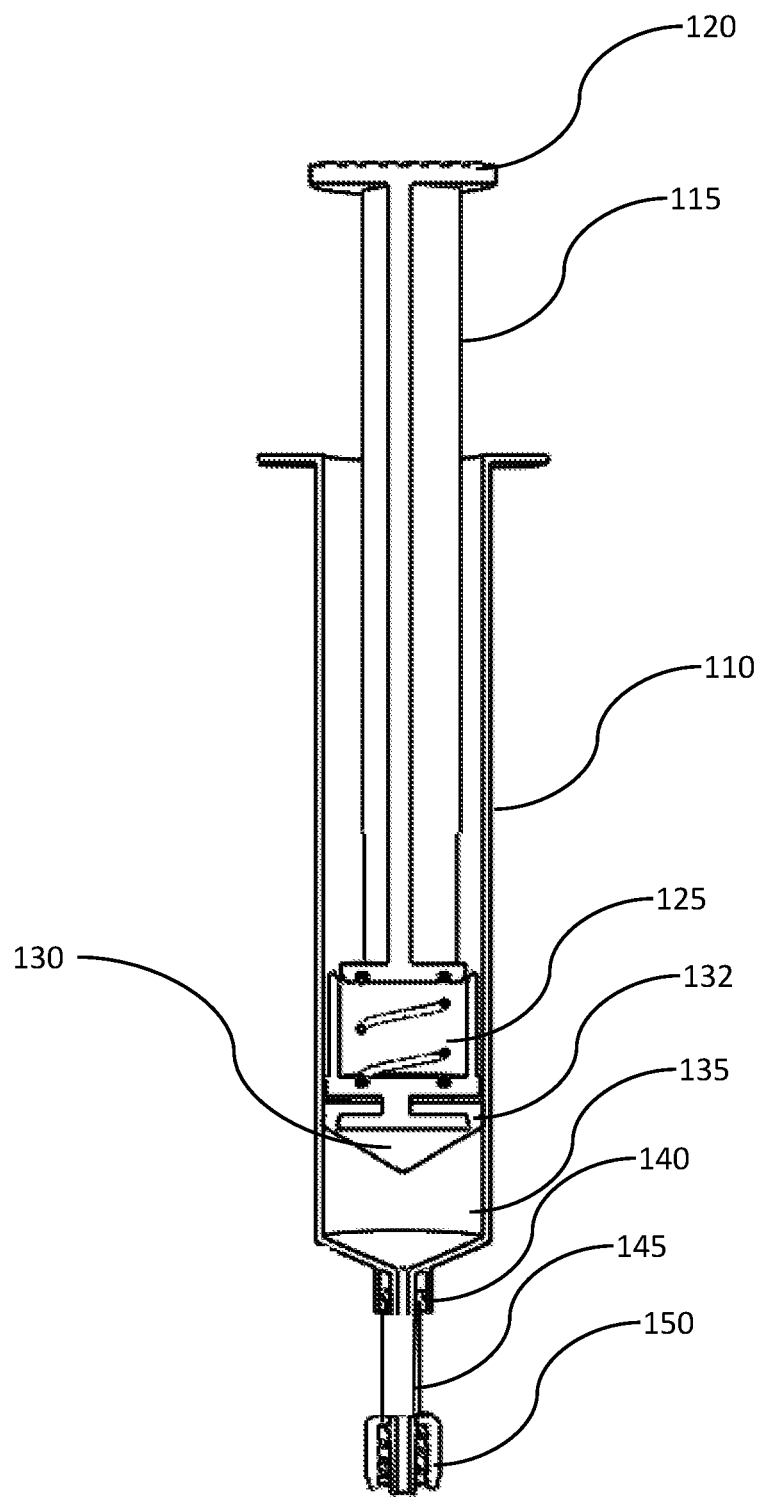
FIG. 1J provides a cross-section view of the fourth embodiment of the cellular therapy infusion device, in accordance with some embodiments of the present invention.

FIGS. 1I and 1J provide side and cross section views, respectively, of a fourth cellular therapy infusion device 103 that is similar to cellular therapy infusion device 100 but does not include a pressure relief system 170 or components thereof. In fourth cellular therapy infusion device 103, pressure/force dampening mechanism 125 and pressure dampening tip 130 are not optional and form a pressure relieving system configured to absorb pressure that may be exerted on a volume of cellular therapy media residing within cellular therapy media reservoir 135 as described herein.

Figure 2:
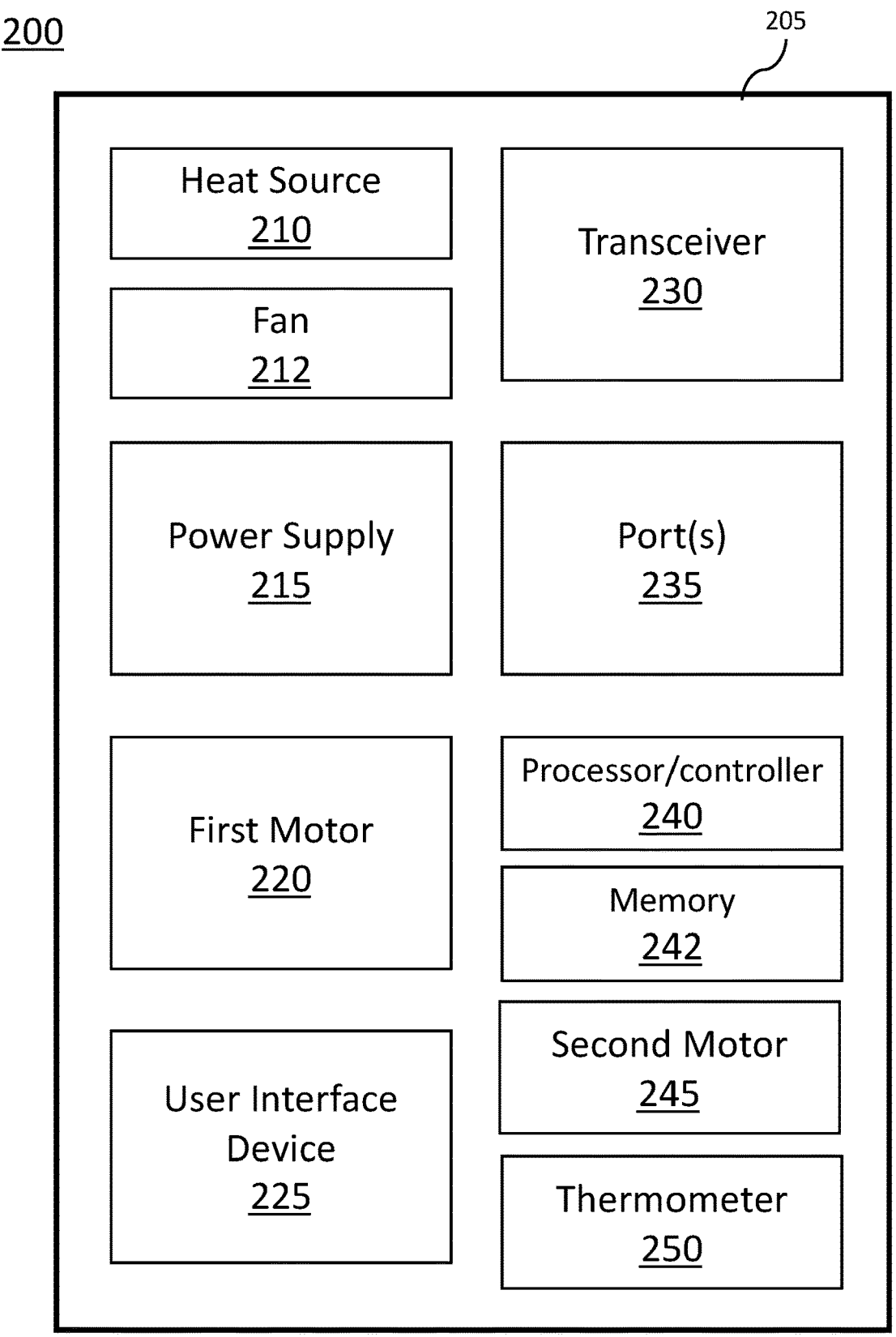
FIG. 2 is a block diagram of a system of components that may be included in a cellular therapy infusion system, in accordance with some embodiments of the present invention.

FIG. 2 is a block diagram of a system 200 of plurality of components that may be included in a cellular therapy infusion system configured to cooperate with cellular therapy infusion device 100, 101, 102, and/or 103 such as cellular therapy infusion system 300 discussed below with regard to FIG. 3. System 200 includes a heat source 210, an optional fan 212, a power supply 215, a first motor 220, a user interface device 225, a transceiver 230, one or more ports 235, a processor/controller 240, a memory 242, a second motor 245, and a thermometer 250; all of which are enclosed in a housing 205. Housing 205 may be configured to house the components of system 200 and may be made from any suitable material (e.g., metal, plastic, etc.).

Heat source 210 may be configured to warm a frozen sample of cellular therapies to a desired temperature and/or maintain a desired temperature for a volume of cellular therapies. Exemplary heat sources 210 include, but are not limited to, resistance coils. Often times, heat source 210 may be configured and/or programmed to bring a volume of cellular therapy media to a temperature of approximately 37 degrees Celsius and/or to maintain a consistent temperature for the volume of cellular therapy media and/or a chamber in which the volume of cellular therapy media is being held. In some embodiments, heat source 210 may include thermometer 250 configured to measure a temperature of, for example, a volume of therapeutic cells, heat source 210, and/or a cellular therapy infusion system and may be configured to provide the temperature to, for example, user interface device 225, transceiver 230, a port 235, and/or processor/controller 245. Fan 212 may be configured to circulate air and/or heat provided by heat source 210 within housing 205, a cellular therapy infusion system, and/or components thereof to achieve and/or maintain a desired temperature within the cellular therapy infusion system or components thereof.

Power supply 215 may be configured to provide electrical power to one or more components of system 200 and/or a cellular therapy infusion system and may be, for example, a battery and/or circuitry configured to couple to an electrical main. First motor 220 and second motor 245 may be configured to rotate and/or move one or more components of a cellular therapy infusion system as will be discussed in greater detail below with regard to FIGS. 3 and 4. First motor 220 and/or second motor 245 may be, for example, a stepper motor.

User interface device 225 may be any device, or combination of devices, that configured to enable a user to monitor an operation of a component of system 200 and/or a cellular therapy infusion system and/or provide instructions (e.g., on/off) to la component of system 200 and/or a cellular therapy infusion system. Exemplary user interface device(s) 225 include, but are not limited to, dials, buttons, a keyboard, display devices, speakers, and touch screens.

Transceiver 230 may be configured to transmit and/or receive communication via, for example, wireless or wired (via e.g., a port 235) communication. Exemplary received communications include, but are not limited to, instructions for operation, parameters for operation (e.g., start/stop times, run time duration, type of therapeutic cells being used, infusion rates, preferred temperature of therapeutic cells, preferred temperature within a cellular therapy infusion system, and/or motion rates). Exemplary transmitted communications include but are not limited to, parameters of operation (e.g., run time duration, temperature of therapeutic cells over time, and/or error conditions). Ports 235 may be configured as, for example, power, user interface, and/or communication ports and may be coupled to, for example, controller/processor 240 and/or memory 242.

Thermometer 250 may be configured to measure a temperature within a cellular therapy infusion system so that it achieves and/or maintains a desired temperature (e.g., 37 degrees Celsius). At times, thermometer 250 may be coupled to processor/controller and/or heat source 210 and activation of heat source 210 may be responsive to a temperature measurement from thermometer 250 that is received by processor/controller 240 (which provides an activation instruction to heat source 210) and/or heat source 210 directly via, for example, a thermocouple or switch.

Processor/controller 240 may be programmed and/or configured to control an operation of one or more components of system 200 such as a rate of rotation of first motor 220, a rate of rotation of second motor 245, a temperature achieved and/or maintained by heat source 210, and/or communications sent out and/or received by transceiver 230. Instructions for operating the processor/controller and/or executing one or more methods disclosed herein may be stored in memory 242. Additionally, or alternatively, processor/controller 240 may be configured to receive instructions pertaining to an operation of system 200 via, for example, user interface device 225, a port 235, and/or transceiver 230. Additionally, or alternatively, processor/controller 240 may be configured to provide information to a user regarding an operation of system 200 via, for example, user interface device 225, a port 235, and/or transceiver 230. Processor/controller 240 may further be configured to precisely control various parameters for infusing the cellular therapy media into a patient such as the thaw rate, temperature, agitation rate, type of agitation (e.g., spinning, rotating, shaking, oscillating, rocking and/or random motion), and/or infusion rate (e.g., a rate of motion for a worm gear and/or a headplate) of the cellular therapy media through cellular therapy infusion device 100 and into a patient. At times, these parameters may be default settings. In some cases, one or more of these parameters may be specific to, for example, a type of cellular therapy, a type of media in which the cellular therapy is suspended, a characteristic of a target tissue for treatment with the cellular therapy, and/or a characteristic of the patient receiving the cellular therapy. In some embodiments, processor/controller 240 may enable a user to override one or more default settings of system 200 via, for example, user interface device 225 and/or a software program running on an external computing device that may be in communication with transceiver 230.

In some embodiments, heat source 210, fan 212, processor/controller 240 and thermometer 250 may cooperate as a thermal equilibrium system so that processor/controller 240 controls the operation of heat source 210 and fan 212 responsively to a temperature (received from thermometer 250) within a cellular therapy infusion system or components thereof to achieve and/or maintain a desired temperature within the cellular therapy infusion system or components thereof.

At times, processor/controller 240 and transceiver 230 may cooperate to communicate with a software application running on, for example, a computer, tablet computer, and/or smart phone. Transceiver 230 may use a wired and/or wireless (e.g., BLUETOOTH) communication protocol to communicate with the software application.

Figure 3:
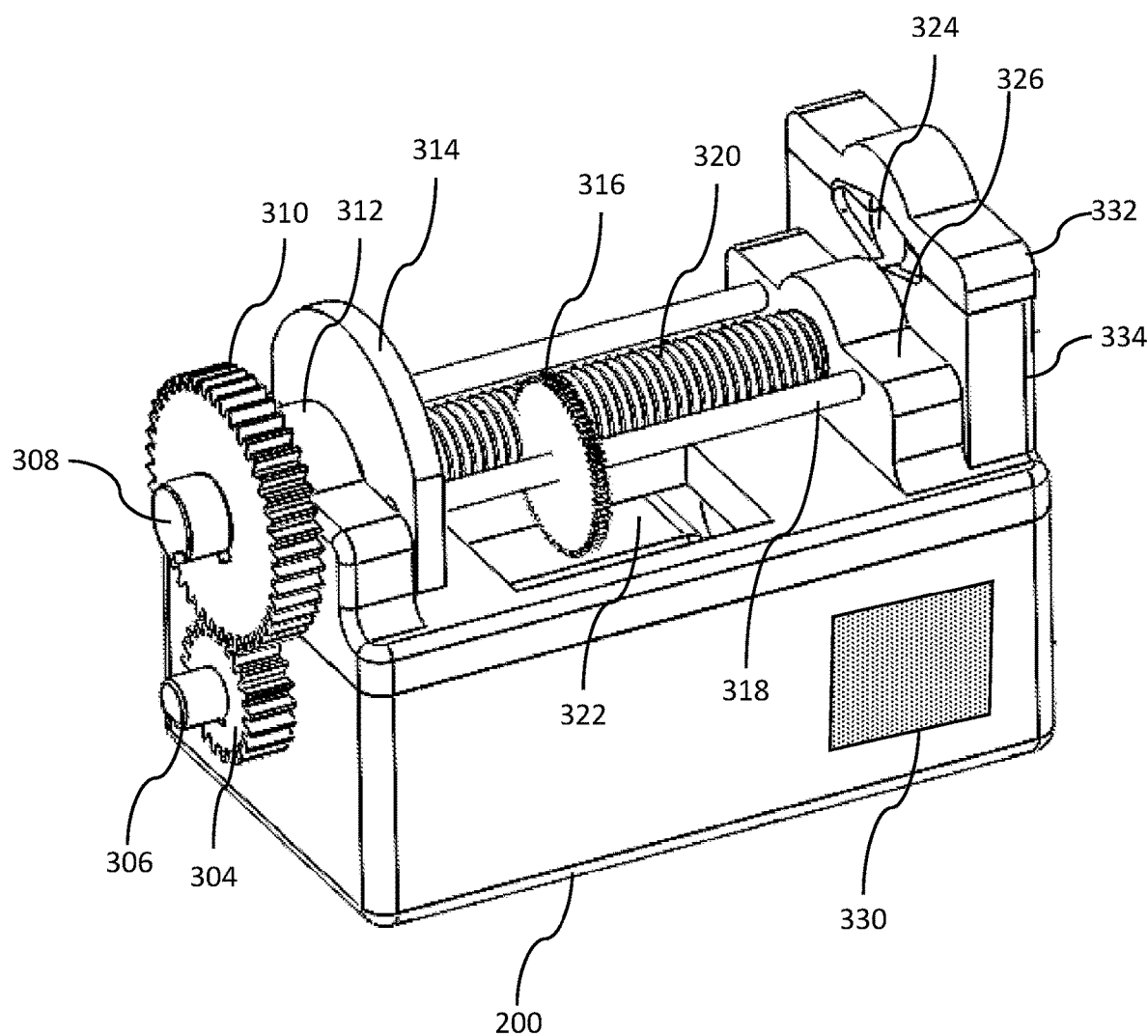
FIG. 3 is a side-perspective view of an exemplary cellular therapy infusion, in accordance with some embodiments of the present invention.

FIG. 3 is a side-perspective view of an exemplary cellular therapy infusion system 300 that includes the internal components of cellular therapy infusion system 200. Cellular therapy infusion system 300 includes a first gear 304 that rotates around a first shaft 306, a second larger gear 310 that rotates around a second shaft 308, a second shaft holder 312, a headplate 314, a rotation gear 316, a rotation shaft 318, a worm gear 320, an infusion tray 322, a catheter exit port 324, a positioning bracket 326, a catheter exit port cover 332, an endplate 334, and a user interface window 330. Headplate 314 may be configured to hold plunger 115 in place via compression of cellular therapy infusion 100, 101, 102, or 103. Infusion tray 322 may be configured to separate cellular therapy infusion device 100, 101, 102, or 103 from cellular therapy infusion system 300 in order to prevent contamination of cellular therapy infusion system 300 by any cellular therapy media that may leak from cellular therapy infusion device 100, 101, 102, or 103.

First shaft 306 may be mechanically coupled to first motor 220. Rotation of first motor 220 may rotate first gear 304. First gear 304 and second gear 310 may be arranged so that teeth and/or gear extensions of first gear 304 and second gear 310 engage with one another as first gear 304 is rotated about first shaft 306. When first gear 304 rotates around first shaft 306, the teeth of first gear 304 may engage with the teeth of second gear 310 and rotational motion of first gear 304 may cause rotation of second gear 310 about second shaft 308. This rotation of second gear 310 may cause worm gear 320 to rotate.

Headplate 314 may be mechanically coupled to worm gear 320 and worm gear may be mechanically coupled to a motor, such as first motor 220. First motor 220 may rotate and this rotation may be translated to worm gear 320, which may translate the rotational motion of first motor 220/worm gear 320 to linear motion of headplate 314. Worm gear 320 may then translate the rotary motion from first motor 220 into linear motion of headplate 314 so that headplate 314 linearly moves from left to right (as oriented in FIG. 3). This linear motion of headplate 314 may act to linearly translate a plunger of a cellular therapy infusion device, such as plunger 115 of cellular therapy infusion device 100, 101, 102, or 103 from a first position to a second position (i.e., plunger 115 is pushed into barrel 110 to push cellular therapy media out of cellular therapy media reservoir 135 and into syringe shaft 145).

Rotation gear 316 may be configured to engage with a corresponding component and/or exterior portion of barrel 110, such as a barrel rotation gear 445 as shown in FIG. 4A and discussed below. Rotation shaft 318 may be mechanically coupled to second motor 245 and may rotate around a center axis via this coupling. Rotation of rotation shaft 318 may also cause rotation of rotation gear 316 about the center axis of rotation shaft 318. When a cellular therapy infusion device 100, 101, 102, and/or 103 is positioned within cellular therapy infusion system 300, an engagement (e.g., friction or gear-driven) between rotation gear 316 and barrel rotation gear 445 may allow for the rotation of barrel 110 about a central axis and this rotation of barrel 110 may agitate cellular therapy suspended in the cellular therapy media of cellular therapy media reservoir 135.

Positioning bracket 326 may hold various components of cellular therapy infusion system 300 such as worm gear 320, rotation shaft 318 in place. Positioning bracket 326 may facilitate/allow for the rotation of worm gear 320 and/or rotation shaft 318 via, for example, a rotating connection (e.g., slip seal) and/or a bearing (e.g., ball bearing).

User interface 330 may be any device, or combination of devices, by which a user may communicate with (e.g., enter instructions and/or receive information) cellular therapy infusion system 330 including, but not limited to a keypad, touch screen, button, display screen, a speaker, and a microphone. User interface 330 may be communicatively, electronically, and/or mechanically coupled to user interface 225.

FIG. 4A is a side-perspective view of an exemplary assembly 400 of cellular therapy infusion system 300 with a cellular therapy infusion device 100, 101, or 102 positioned therein so that syringe shaft 145 is positioned proximate to and/or within catheter exit port 324. FIG. 4B is a close-up view of a portion the exemplary cellular therapy infusion system 300 with a cellular therapy infusion device 100, 101, or 102 positioned therein that shows how syringe shaft 145 couples to a catheter lead 425 via catheter coupling 150. Cather lead 425 is coupled to a catheter tube 430 that is in communication with syringe shaft 150 for delivery of cellular therapy media to the patient. Once the catheter coupling 150, catheter lead 425, and catheter 430 are assembled, the assembly may rest within and be held in place by catheter exit port 324 as shown in FIG. 4B.

Figure 4C:
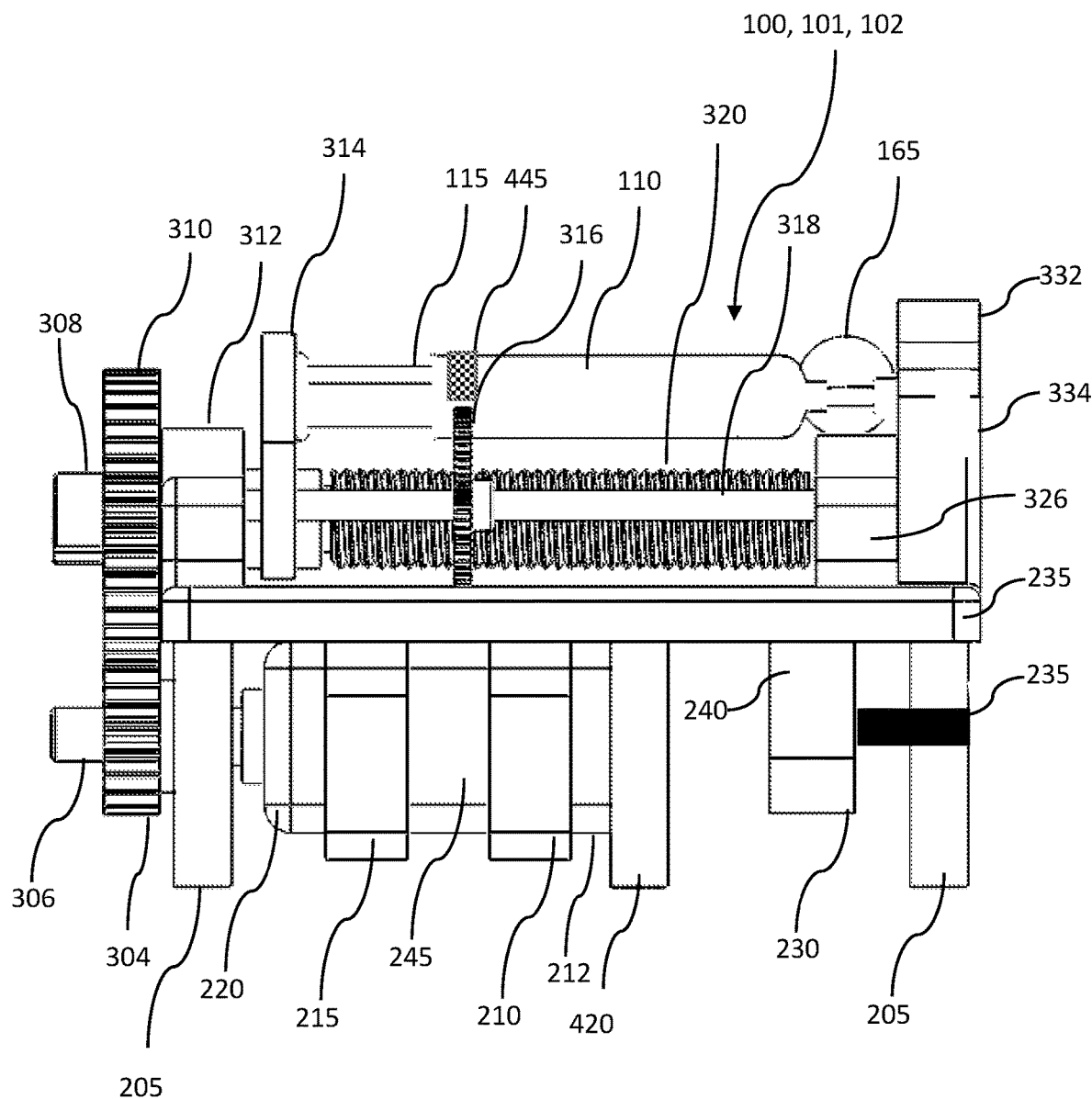
FIG. 4C is a cut-away view of the exemplary cellular therapy infusion system with a cellular therapy infusion device positioned therein of FIG. 4A with a housing for a base of the cellular therapy infusion system therefrom, in accordance with some embodiments of the present invention.

FIG. 4C is a side cut-away view of exemplary cellular therapy infusion system 300 with cellular therapy infusion device 100, 101, or 102 positioned therein in a manner similar FIG. 4A with a front panel of housing 205 removed from a base of cellular therapy infusion system 300. FIG. 4C shows one exemplary arrangement of the components of system 200 within the base of cellular therapy infusion system 300. In particular, FIG. 4C shows how first motor 220 has first shaft 306 extending therefrom so that rotation of first shaft 306 by first motor 220 may be translated to first gear 304 as disclosed herein. First motor 220 may be held in place by a bracket 420 that is attached to a base plate 435. Second shaft holder 312, positioning bracket 326, and/or endplate 334 may also be attached to a base plate 435. In some embodiments, bracket 420 may be configured as a heat shield that shields processor/controller 240, transceiver 230, communication interface 330 (not shown) and/or port(s) 235 from heat generated by heat source 210, first motor 220, and/or second motor 245. As may be seen in FIG. 4C, port(s) 235 are physically coupled to controller/processor 240.

Figure 5A:
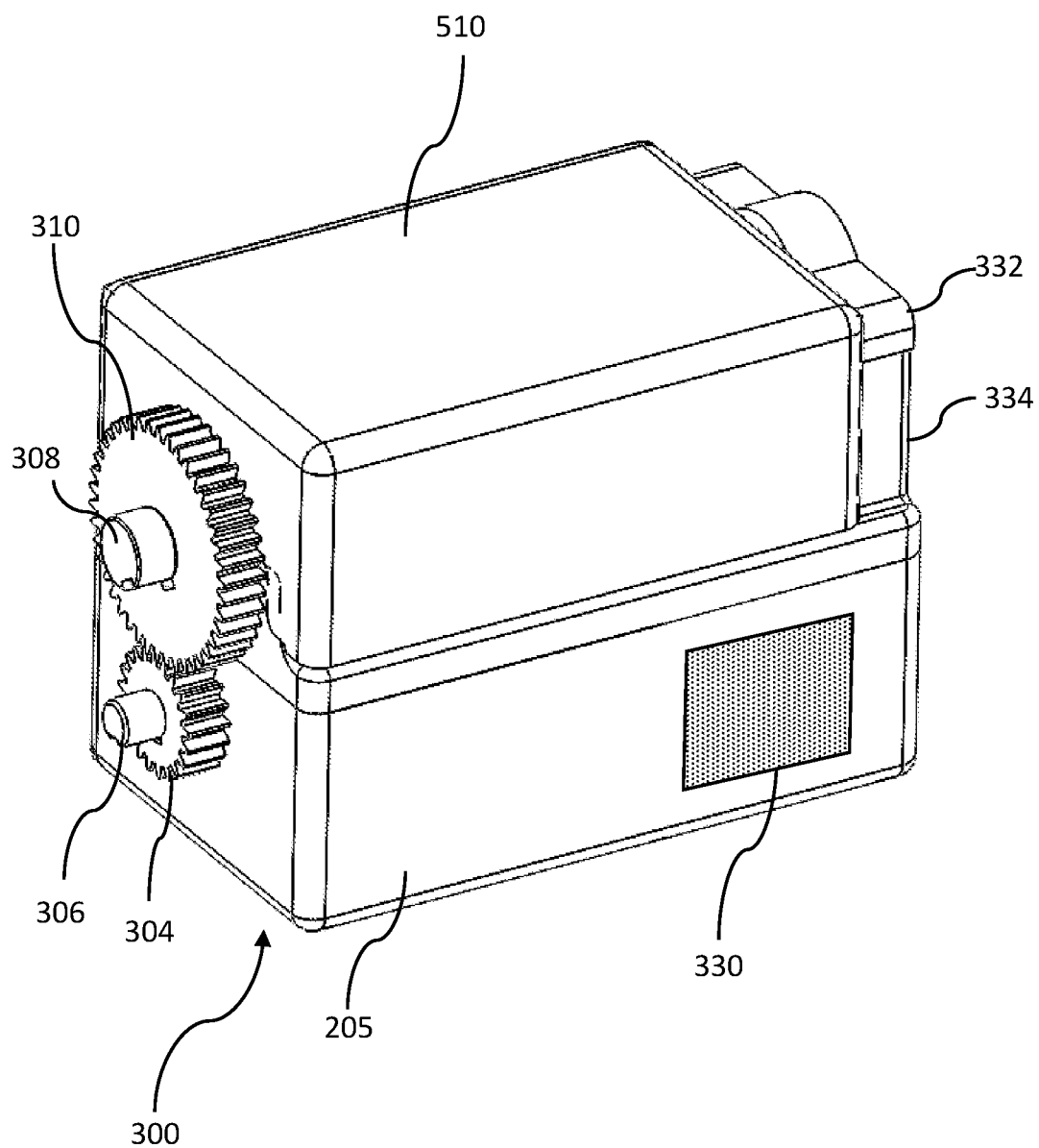
FIG. 5A is a rear perspective view of the exemplary cellular therapy infusion system of FIG. 3 or the exemplary cellular therapy infusion system with a cellular therapy infusion device positioned therein of FIG. 4A with a lid positioned thereon, in accordance with some embodiments of the present invention.

In addition, heat source 210 may be coupled to base plate 435 and, in some embodiments, base plate 435 may dissipate and/or spread heat generated by heat source 210 toward cellular therapy infusion device 100, 101, or 102 and/or within a portion of cellular therapy infusion system 300 that houses cellular therapy infusion device 100, such as an area under a lid like lid 510 as shown in FIG. 5A. Lid 510 may reduce cellular therapy infusion device's 100 interaction with ambient air and/or retain thermal equilibrium within a portion of cellular therapy infusion system 300 covered by lid 510 when lid 510 is closed. In some embodiments, lid 510 may be transparent, or semi-transparent, to that, for example, internal components and/or motion thereof (e.g., motion of worm gear 320, motion of headplate 314, and/or motion of plunger end 120 and/or plunger 115 as headplate 314 linearly translates toward barrel 110 to, for example, push a volume of cellular therapy media from cellular therapy media reservoir 135, through syringe shaft 145, and out to catheter 430.

Figure 4D:
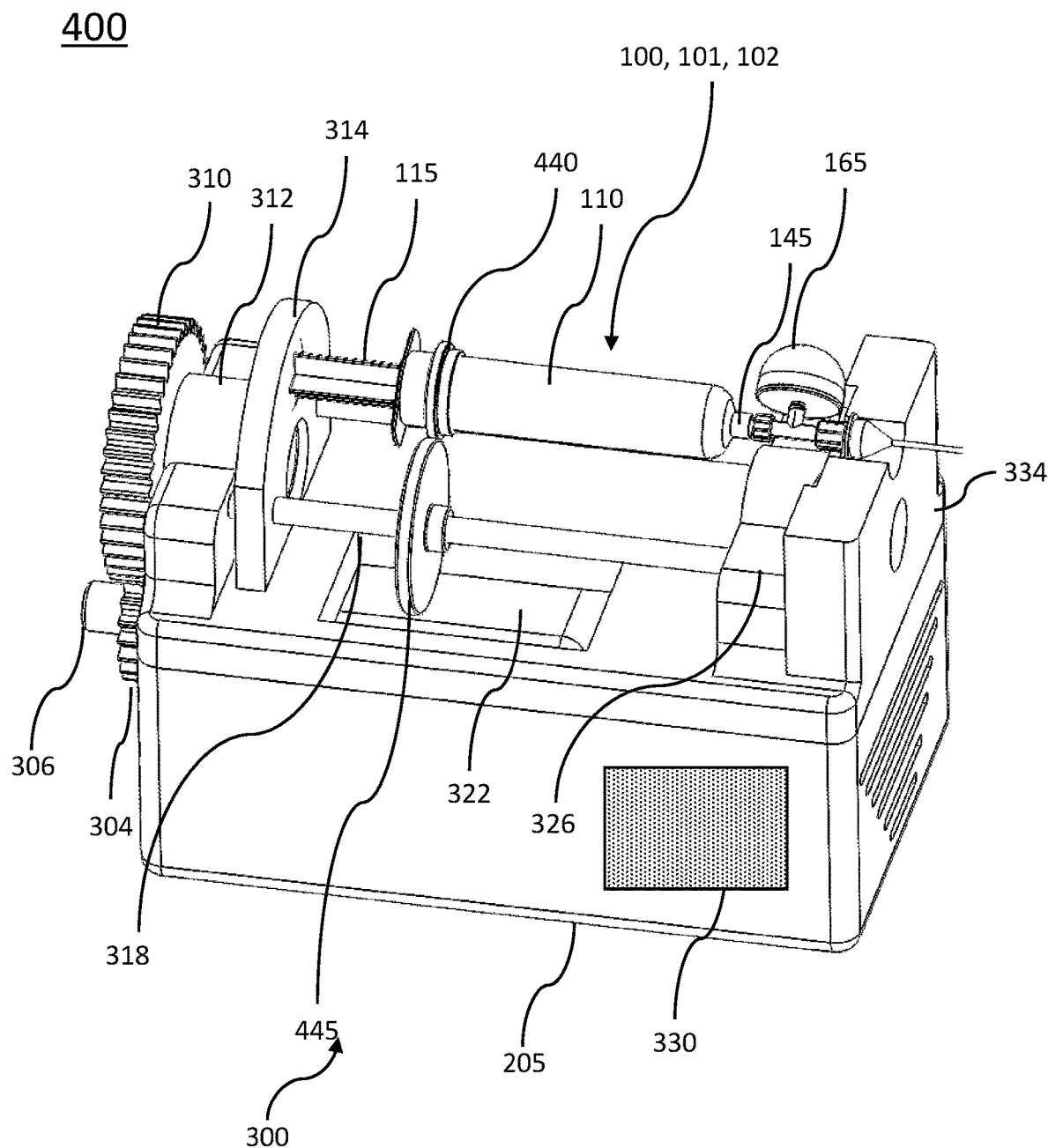
FIG. 4D is a side-perspective view of another exemplary cellular therapy infusion system with another cellular therapy infusion device positioned therein, in accordance with some embodiments of the present invention.

FIG. 4D is a side-perspective view an exemplary assembly 401 of an alternative embodiment of alternate embodiment of a cellular therapy infusion system 301 with a cellular therapy infusion device 100, 101, or 102 positioned therein that includes a gasket 440 positioned on an exterior surface of barrel 110. Cellular therapy infusion system 301 and cellular therapy infusion device 101 are similar to cellular therapy infusion system 300 and cellular therapy infusion device 100, 101, or 102, respectively, with the exception that rotation gear 316 and corresponding barrel rotation gear 445 are replaced with a compression- and/or friction-driven system for rotation of barrel 110 (as opposed to a gear driven system for rotation gear 316 and barrel rotation gear 445) comprising a rotation drive wheel 445 positioned on rotation shaft 318 and a corresponding smooth gasket 440 positioned on barrel 110. Smooth gasket 440 may encircle barrel 110 and may be made from a material (e.g., rubber, latex, silicon) that abuts and engages an outer edge of rotation drive wheel 445. In some embodiments, an outer edge of rotation drive wheel 445 may be covered with a material (e.g., rubber, latex, silicon) that abuts and/or engages with gasket 440 as rotation drive wheel 445 rotates due to rotation of rotation shaft 318. As rotation drive wheel 445 turns because of rotational motion of rotation shaft 318, barrel 110 may be rotated around, for example, barrel/shaft coupling 140 to agitate cellular therapy media contained in cellular therapy media reservoir 135, which may prevent adhesion of cellular therapy to a wall, or surface, within cellular therapy media reservoir 135 and/or of cellular therapy infusion device 100, 101, or 102.

Figure 5B:
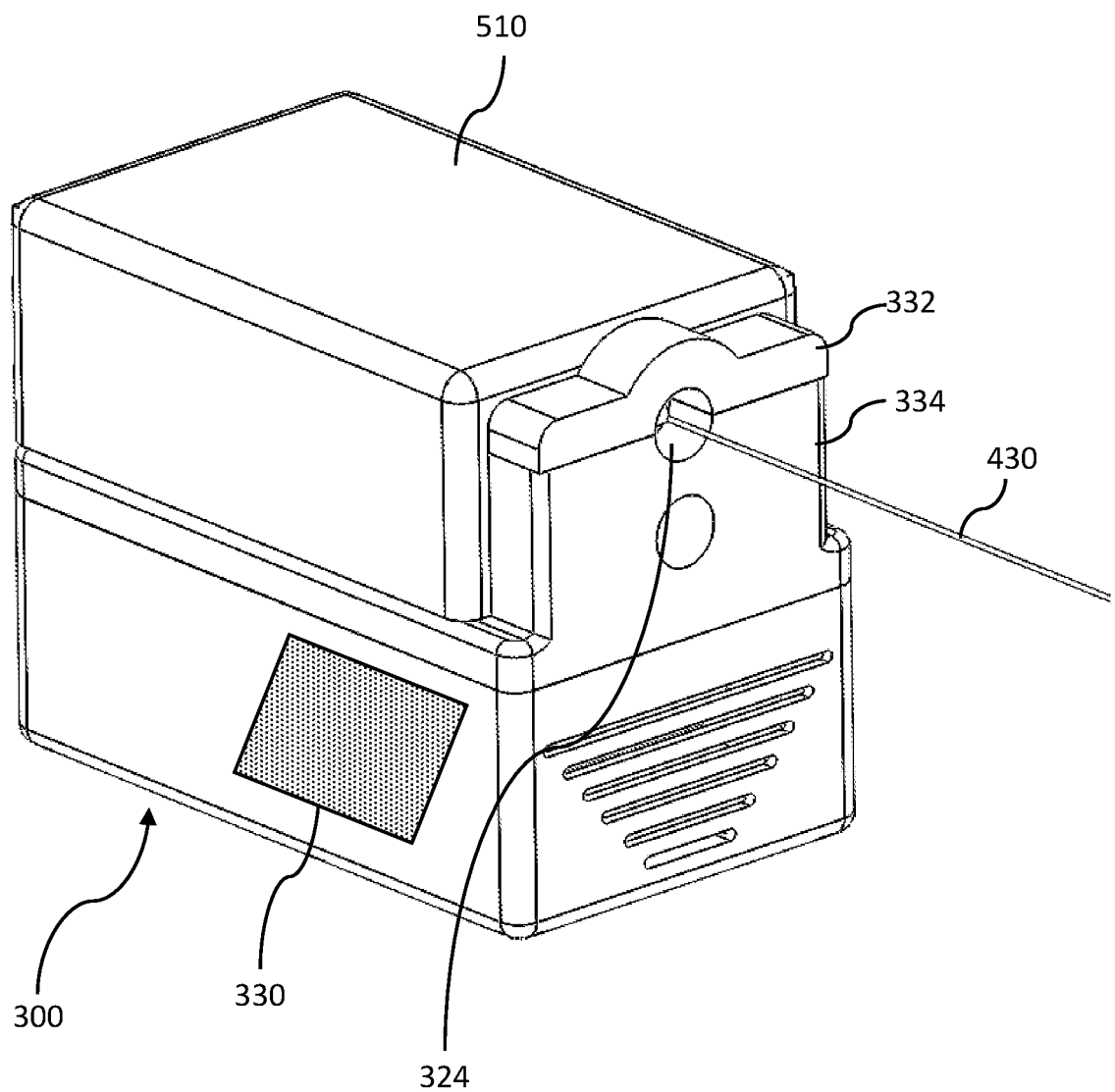
FIG. 5B is a front perspective view of the exemplary cellular therapy infusion system with a cellular therapy infusion device positioned therein of FIG. 4A with a lid positioned thereon and a catheter coupled to the cellular therapy infusion device and extending through a catheter exit port, in accordance with some embodiments of the present invention.

FIG. 5A is a rear perspective view and FIG. 5B is a front perspective view of cellular therapy infusion system 300 with lid 510 positioned thereon. In the embodiment of FIG. 5A, lid 510 covers cellular therapy infusion device 100, 101, or 102 as well as second shaft holder 312, headplate 314, rotation gear 316, rotation shaft 318, worm gear 320, infusion tray 322, positioning bracket 326. In the embodiment of FIGS. 5A and 5B, first shaft 306, first gear 304, second shaft 308, second gear 310, catheter exit port cover 332, and endplate 334 may reside outside lid 510 when lid 510 is closed. In other embodiments, first shaft 306, first gear 304, second shaft 308, and/or second gear 310 may reside within housing 205 and/or lid 510 (when lid 510 is closed). As may be seen in FIG. 5B catheter 430 may extend out of catheter exit port 324 and navigated into patient anatomy so that the cellular therapy may be delivered to patient tissue. In some embodiments, the delivery device may be, for example, catheter 430 itself when, for example, an end of catheter 430 not coupled to catheter lead 425 is inserted into, for example, a patient artery and/or an endoscope. Additionally, or alternatively, catheter 430 may be coupled to a delivery tip such as a flexible needle, specifically configured to deliver cellular therapy directly to tissue (e.g., an organ or muscle).

In some embodiments, the systems and/or devices disclosed herein may be modular in that the cellular therapy infusion device 100, 101, 102, and/or 103 may be separate from cellular therapy infusion system 300. In these embodiments, cellular therapy infusion devices 100, 101, 102, and/or 103 may be configured for one-time use while cellular therapy infusion system 300 may be configured for use with multiple cellular therapy infusion devices 100, 101, 102, and/or 103 over time.

Although FIGS. 4A, 4B, 4C, and 4D show cellular therapy infusion system 400 with exemplary first, second, or third cellular therapy infusion device 100, 101, 102, this need not always be the case. Cellular therapy infusion system 400 may cooperate with other, alternative, cellular therapy infusion devices such as fourth cellular therapy infusion device 103.

Figure 6:
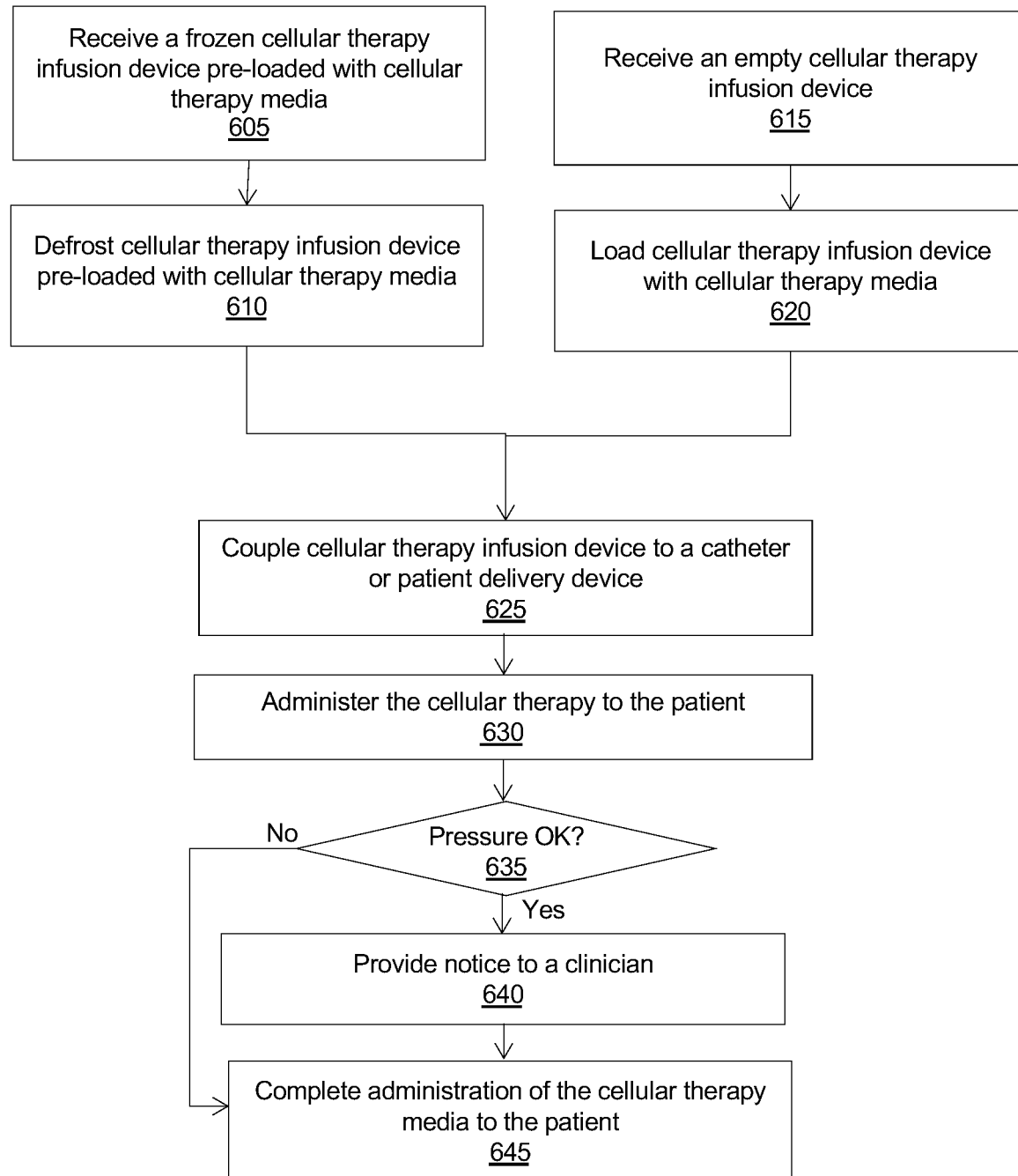
FIG. 6 is a flowchart illustrating a process for manually using a cellular therapy infusion device, in accordance with some embodiments of the present invention.

The cellular therapy infusion devices disclosed herein may be used manually (via manually depressing plunger 115 within barrel 110) and/or via a cellular therapy infusion system such at the cellular therapy infusion systems disclosed herein. For example, FIG. 6 provides a process 600 for manually using a cellular therapy infusion device like cellular therapy infusion device 100, 101, 102, and/or 103 that is either via a frozen cellular therapy infusion device (e.g., cellular therapy infusion device 100) pre-loaded with a volume of cellular therapy media or an empty cellular therapy infusion device that is then loaded with cellular therapy media for administration to a patient via, for example, pulling plunger 115 away from syringe shaft 145 while an open tip of syringe shaft is submerged in cellular therapy media. The vacuum caused by pulling plunger 115 away from syringe shaft 145 will draw cellular therapy media into syringe shaft 145 and pressure relief system 170, pressure/force dampening mechanism 125, and/or pressure dampening tip 130 may act to maintain a preferred level of pressure within the cellular therapy infusion device while cellular therapy media is being drawn into cellular therapy media reservoir 135.

More particularly, in step 605, a frozen cellular therapy infusion device pre-loaded with a volume of cellular therapy media is received by, for example, a clinician or staff member (e.g., nurse, lab technician, or doctor) and the frozen cellular therapy infusion device is defrosted (step 610) until it achieves a desired temperature (e.g., 25-40 degrees Celsius) via any acceptable defrosting means. Alternatively, in step 615, an empty cellular therapy infusion device may be received and loaded with a volume of cellular therapy (step 620).

Then, following either step 610 or 620, the cellular therapy infusion device may be coupled to a patient delivery device such as catheter 430 via, for example, catheter lead 425. The volume of cellular therapy media may then be administered to the patient (step 625) via, for example, manual depression of plunger 115 within barrel 110 by the clinician.

Figure 7:
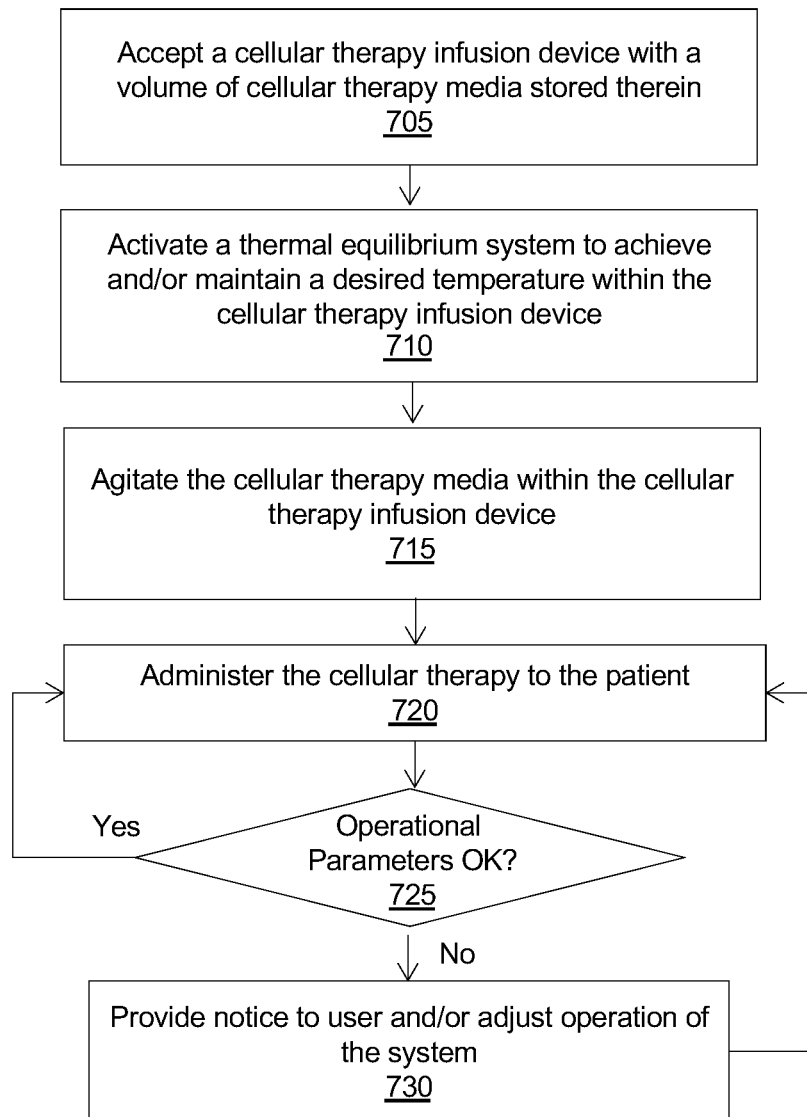
FIG. 7 is a flowchart illustrating a process for using an assembly of a cellular therapy infusion system and cellular therapy infusion device to administer a volume of cellular therapy media to a patient, in accordance with some embodiments of the present invention.

In another example, FIG. 7 provides a process 700 for using an assembly of a cellular therapy infusion system and cellular therapy infusion device such as assembly 400 of cellular therapy infusion system 300 cellular therapy infusion system 100. The assembly may have a lid such as lid 510 to assist with achieving and/or maintaining thermal equilibrium within a chamber of cellular therapy infusion system that holds the cellular therapy infusion device. In some embodiments, the cellular therapy infusion device may be frozen and pre-loaded with a volume of cellular therapy media or may be a cellular therapy infusion device that was loaded with cellular therapy media for administration to a patient.

Initially, in step 705, a cellular therapy infusion device with a volume of cellular therapy media therein may be received by the cellular therapy infusion system. Often step 705 may be executed by a clinician or use placing the cellular therapy infusion device into the cellular therapy infusion system as shown in, for example, FIGS. 4A-4D and a closing a lid of the cellular therapy infusion system (e.g., lid 510). Then, in step 710, a thermal equilibrium system of the cellular therapy infusion system may be activated to achieve and/or maintain a desired temperature (e.g., 25-40 degrees Celsius) within the cellular therapy infusion system. Step 710 may be executed via, for example, a user's interaction with a user interface such as user interface window 330. Exemplary thermal equilibrium system systems include, but are not limited to, a heat source like heat source 210, a fan like fan 212, a thermometer like thermometer 250, and/or a processor and/or controller like processor/controller 240. Additionally, or alternatively, step 710 may be executed automatically by the cellular therapy infusion system that may, in some cases, be responsive to a user action such as turning the cellular therapy infusion system on, detecting the presence of a cellular therapy infusion device within the cellular therapy infusion system, and/or detecting an action (e.g., closing of a lid) that indicates that a cellular therapy infusion device may be resident within the cellular therapy infusion device.

In step 715, the cellular therapy media within the cellular therapy infusion device may be agitated in order to, for example, prevent the cellular therapy from adhering to walls of the cellular therapy infusion device. In some embodiments, step 715 may be executed by, for example, rotation of a barrel (e.g., barrel 110) of a cellular therapy infusion device as, for example, explained herein.

In step 720, the cellular therapy infusion system may administer the cellular therapy to the patient. Step 720 may be executed via, for example, depressing plunger 115 within barrel 110 by movement of a plunger depressing mechanism and/or system such as headplate 314. Movement of headplate 314 may be facilitated by mechanical cooperation between first motor 220 and worm gear 320 as disclosed herein.

Optionally, in step 725, one or more operational parameter feedback measurements may be taken and, if the feedback indicates that the cellular therapy infusion device is working within defined, or preferred, parameters, execution of step 720 may continue until administration of the cellular therapy is complete. When the feedback indicates that the cellular therapy infusion device is not working within defined, or preferred, parameters, a notice (e.g., audible beep, flashing light, or written message) may be provided to the user indicating an error condition and/or one or more operations (e.g., heat source, fan, processor/controller, first motor 220, and/or second motor 245) of the cellular therapy infusion system may be responsively adjusted. Exemplary operational parameter feedback measurements include, but are not limited to, pressure within the cellular therapy infusion device and/or a component coupled thereto (e.g., a catheter) and/or temperature within the cellular therapy infusion system.

We claim:

1. A cellular therapy infusion device comprising:
    a barrel, sized and shaped to accept insertion of a plunger therein and contain a volume of cellular therapy media;
    a syringe shaft, a first end of the syringe shaft being physically coupled to and in liquid communication with the barrel and a second end of the syringe shaft including a catheter coupling configured to couple to a catheter;
    the plunger positioned within the barrel at a first position, an assembly of the plunger and the barrel being configured so that when the plunger is translated from the first position to a second position, a force is applied to the volume of cellular therapy media that pushes the cellular therapy media from the barrel into the syringe shaft;
    a pressure relief system including a diaphragm, the pressure relief system being physically coupled to and in communication with the syringe shaft, wherein the diaphragm is configured to expand in shape when a force is exerted thereon and thereby absorb pressure within at least one of the syringe shaft and the barrel.

2. The cellular therapy infusion device of claim 1, wherein the syringe shaft is physically coupled to the barrel via a coupling that is configured to allow the barrel to rotate around the syringe shaft while the syringe shaft remains stationary.

3. The cellular therapy infusion device of claim 1, wherein an internal surface of at least one of the barrel, the plunger, and the syringe shaft is coated with an adhesion-resistant coating.

4. The cellular therapy infusion device of claim 1, wherein the plunger includes a pressure dampening tip.

5. The cellular therapy infusion device of claim 1, wherein a barrel rotation mechanism encircles a portion of an exterior surface of the barrel, the barrel rotation mechanism being configured and positioned to cooperate with a corresponding rotation mechanism of a cellular therapy infusion system to agitate the volume of cellular therapy media contained in the barrel.

6. The cellular therapy infusion device of claim 1, wherein the barrel contains cellular therapy media that expands during a freezing process of the cellular therapy infusion device with the volume of cellular therapy media stored therein, wherein the pressure relief system absorbs a portion of the cellular therapy media that expands due to freezing of the cellular therapy media said expansion.

7. The cellular therapy infusion device of claim 1, wherein a material used in the construction of the barrel, the syringe shaft, and the plunger have similar freezing and thawing properties.

8. The cellular therapy infusion device of claim 1, wherein the plunger further includes a sealing mechanism configured to interface with, and exert force on, an internal surface of the barrel thereby sealing the volume of cellular therapy media within the barrel, the force exerted by the sealing mechanism on the internal surface of the barrel being sufficient to prevent expansion of a frozen volume of cellular therapy media beyond the sealing mechanism.

9. A cellular therapy infusion device comprising:
    a barrel, sized and shaped to accept insertion of a plunger therein and contain a volume of cellular therapy media;
    a syringe shaft, a first end of the syringe shaft being physically coupled to and in liquid communication with the barrel and a second end of the syringe shaft including a catheter coupling configured to couple to a catheter, wherein the syringe shaft is physically coupled to the barrel via a coupling that is configured to allow the barrel to rotate around the syringe shaft while the syringe shaft remains stationary; and
    the plunger positioned within the barrel at a first position, an assembly of the plunger and the barrel being configured so that when the plunger is translated from the first position to a second position, a force is applied to the volume of cellular therapy media, the force pushing the cellular therapy media from the barrel into the syringe shaft; and
    a pressure relief system including a diaphragm, the pressure relief system being physically coupled to and in communication with the syringe shaft, wherein the diaphragm is configured to expand in shape when a force is exerted thereon and thereby absorb pressure within at least one of the syringe shaft and the barrel.

10. The cell therapy delivery device of claim 9, wherein rotation of the barrel agitates the cellular therapy media thereby preventing adhesion of cellular therapies included within the cellular therapy media to a surface of the barrel.

11. The cellular therapy infusion device of claim 9, wherein the first end of the syringe shaft is physically coupled to the barrel via a slip seal connector that allows the barrel to rotate about an axis while keeping the syringe shaft stationary.

12. The cellular therapy infusion device of claim 9, wherein an internal surface of at least one of the barrel, the plunger, and the syringe shaft is coated with an adhesion-resistant coating.

13. The cellular therapy infusion device of claim 12, wherein the plunger includes a pressure dampening tip.

14. The cellular therapy infusion device of claim 9, wherein a barrel rotation mechanism encircles a portion of an exterior surface of the barrel, the barrel rotation mechanism being configured and positioned to cooperate with a corresponding rotation mechanism of a cellular therapy infusion system to agitate the volume of cellular therapy media contained in the barrel.

15. The cellular therapy infusion device of claim 9, wherein a material used in the construction of the barrel, the syringe shaft, and the plunger have similar freezing and thawing properties.

16. The cellular therapy infusion device of claim 9, wherein the plunger further includes a sealing mechanism configured to interface with, and exert force on, an internal surface of the barrel thereby sealing the volume of cellular therapy media within the barrel, the force exerted by the sealing mechanism on the internal surface of the barrel being sufficient to prevent expansion of a frozen volume of cellular therapy media beyond the sealing mechanism.

17. A cellular therapy infusion system comprising:
a cellular therapy infusion device comprising:
- a barrel, sized and shaped to accept insertion of a plunger therein and contain a volume of cellular therapy media;
- a syringe shaft, a first end of the syringe shaft being physically coupled to and in liquid communication with the barrel and a second end of the syringe shaft including a catheter coupling configured to couple to a catheter;
- the plunger positioned within the barrel at a first position, an assembly of the plunger and the barrel being configured so that when the plunger is translated from the first position to a second position, a force is applied to the volume of cellular therapy media that pushes the cellular therapy media from the barrel into the syringe shaft; and
- a pressure relief system including a diaphragm, the pressure relief system being physically coupled to and in communication with the syringe shaft, wherein the diaphragm is configured to expand in shape when a force is exerted thereon and thereby absorb pressure within at least one of the syringe shaft and the barrel;

an endplate for accepting and holding the cellular therapy infusion device positioned therein in place, the endplate including a catheter exit port configured, arranged, and positioned to allow the catheter coupled to the cellular therapy infusion device to exit the cellular therapy infusion system via the catheter exit port;

a motor for moving a headplate mechanically coupled thereto;

the headplate mechanically coupled to the motor and configured to apply the steady compressive force to the plunger responsively to movement of the motor, the steady compressive force translating the plunger from the first position to the second position.

18. The cellular therapy infusion system of claim 17, further comprising: a thermometer configured to measure a temperature within the cellular therapy infusion system; and a heat source, the heat source being coupled to the thermometer, wherein the heat source is configured to generate heat responsively to a temperature measured by the thermometer.

19. The cellular therapy infusion system of claim 17, further comprising: an agitation mechanism configured to agitate the volume of cellular therapy media.

20. A cellular therapy infusion device comprising:
- a barrel, sized and shaped to accept insertion of a plunger therein and contain a volume of cellular therapy media;
- a syringe shaft, a first end of the syringe shaft being physically coupled to and in liquid communication with the barrel and a second end of the syringe shaft including a catheter coupling configured to couple to a catheter;
- the plunger positioned within the barrel at a first position, an assembly of the plunger and the barrel being configured so that when the plunger is translated from the first position to a second position, a force is applied to the volume of cellular therapy media that pushes the cellular therapy media from the barrel into the syringe shaft;
- a pressure relief system including a diaphragm, the pressure relief system being physically coupled to and in communication with the syringe shaft, the diaphragm being configured to expand in shape to accommodate volumetric expansion of the volume of cellular therapy media as the volume of cellular therapy media transitions from a liquid state to a frozen state.

21. The cellular therapy infusion device of claim 20, wherein a material used in the construction of the barrel, the syringe shaft, and the plunger have similar freezing and thawing properties.

22. The cellular therapy infusion device of claim 20, wherein the plunger further includes a sealing mechanism configured to interface with, and exert force on, an internal surface of the barrel thereby sealing the volume of cellular therapy media within the barrel, the force exerted by the sealing mechanism on the internal surface of the barrel being sufficient to prevent expansion of a frozen volume of cellular therapy media beyond the sealing mechanism.

* * * * *